(12) United States Patent
Nakagaki et al.

(10) Patent No.: US 9,335,277 B2
(45) Date of Patent: May 10, 2016

(54) REGION-OF-INTEREST DETERMINATION APPARATUS, OBSERVATION TOOL OR INSPECTION TOOL, REGION-OF-INTEREST DETERMINATION METHOD, AND OBSERVATION METHOD OR INSPECTION METHOD USING REGION-OF-INTEREST DETERMINATION METHOD

(75) Inventors: Ryo Nakagaki, Tokyo (JP); Takehiro Hirai, Tokyo (JP); Kenji Obara, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 57 days.

(21) Appl. No.: 14/239,653

(22) PCT Filed: Jul. 9, 2012

(86) PCT No.: PCT/JP2012/067419
§ 371 (c)(1),
(2), (4) Date: Feb. 19, 2014

(87) PCT Pub. No.: WO2013/035421
PCT Pub. Date: Mar. 14, 2013

(65) Prior Publication Data
US 2014/0198975 A1  Jul. 17, 2014

(30) Foreign Application Priority Data

Sep. 7, 2011  (JP) .................. 2011-194506

(51) Int. Cl.
*G06K 9/00* (2006.01)
*G01N 21/95* (2006.01)
(Continued)

(52) U.S. Cl.
CPC ........ *G01N 21/9501* (2013.01); *G01N 23/2251* (2013.01); *G01N 2223/6116* (2013.01); *H01L 22/12* (2013.01)

(58) Field of Classification Search
CPC .................. G01N 21/9501; G01N 21/95607; G06T 7/001; G06T 7/0004; G06T 2207/30148; H01J 37/26
See application file for complete search history.

(56) References Cited

U.S. PATENT DOCUMENTS 6,553,323 B1 * 4/2003 Obara et al. .................... 702/35
6,898,305 B2 * 5/2005 Hiroi et al. .................... 382/149
(Continued)

FOREIGN PATENT DOCUMENTS

JP  2010-067533 A   3/2010
JP  2010-258013 A  11/2010
(Continued)

OTHER PUBLICATIONS

International Search Report, w/ English translation thereof, issued in International Application No. PCT/JP2012/067419 dated Oct. 16, 2012.

*Primary Examiner* — Amir Alavi
(74) *Attorney, Agent, or Firm* — McDermott Will & Emery LLP

(57) ABSTRACT

A region-of-interest determination apparatus includes: a calculation unit and a region determination unit. The calculation unit calculates a degree of a defect based on at least a plurality of kinds of defect attribute information regarding defect data. The defect data includes an image corresponding to a defect position detected on a specimen by inspection thereof or an image corresponding to a defect position predicted to be likely to develop a defect on the specimen, where both images are obtained by imaging. The region determination unit extracts the defect data of which the degree is higher than a predetermined level, and determines the region to be observed or inspected on the specimen based on the extracted defect data.

15 Claims, 17 Drawing Sheets

(51) Int. Cl.
 *G01N 23/225* (2006.01)
 *H01L 21/66* (2006.01)

(56) References Cited

U.S. PATENT DOCUMENTS

| | | | |
|---|---|---|---|
| 6,902,855 B2 | 6/2005 | Peterson et al. | |
| 7,170,593 B2 * | 1/2007 | Honda et al. | 356/237.1 |
| 7,388,979 B2 * | 6/2008 | Sakai et al. | 382/149 |
| 7,932,493 B2 * | 4/2011 | Harada et al. | 250/306 |
| 2007/0103893 A1 * | 5/2007 | Tanaka | 362/138 |
| 2011/0163230 A1 | 7/2011 | Hiroi et al. | |
| 2012/0257041 A1 | 10/2012 | Nakagaki et al. | |
| 2013/0248709 A1 * | 9/2013 | Yamamoto et al. | 250/309 |
| 2014/0198975 A1 * | 7/2014 | Nakagaki et al. | 382/149 |

FOREIGN PATENT DOCUMENTS

| | | |
|---|---|---|
| JP | 2011-119471 A | 6/2011 |
| WO | 2010/091307 A2 | 8/2010 |
| WO | 2011/036846 A1 | 3/2011 |

* cited by examiner

TYPICAL CHIP MAP

FIG. 7

| SELECTED CHIPS | PARTIAL REGIONS | DEFECT TYPE | PATTERN GROUPING | REPRESENTATIVE EXAMPLE | DATA COUNT | SCORE |
|---|---|---|---|---|---|---|
| INSIDE SELECTED CHIPS | INSIDE REGION | PATTERN-SHORT/ PATTERN-OPEN | GROUP 1 | | 185 | 10000 |
| | | | GROUP 2 | | 116 | 10000 |
| | | | GROUP 3 | | 62 | 10000 |
| | | | OTHERS | — | 98 | 5000 |
| | | OTHERS | | — | 39 | 500 |
| | OUTSIDE REGION | — | | — | 113 | 0 |
| OUTSIDE | | — | | — | 388 | 0 |

WAFER LAYOUT AND SELECTED CHIP

CHIP MAP AND PARTIAL REGIONS

CHIP MAP OF REGION 1

CHIP MAP OF REGION 4

REGION-OF-INTEREST DETERMINATION APPARATUS, OBSERVATION TOOL OR INSPECTION TOOL, REGION-OF-INTEREST DETERMINATION METHOD, AND OBSERVATION METHOD OR INSPECTION METHOD USING REGION-OF-INTEREST DETERMINATION METHOD

RELATED APPLICATIONS

This application is the U.S. National Phase under 35 U.S.C. §371 of International Application No. PCT/JP2012/067419, filed on Jul. 9, 2012, which in turn claims the benefit of Japanese Application No. 2011-194506, filed on Sep. 7, 2011 the disclosures of which Applications are incorporated by reference herein.

TECHNICAL FIELD

The present invention relates to wafer defect inspection performed in a front-end process in which device patterns are fabricated on a semiconductor wafer serving as a specimen, and to pattern metrology.

BACKGROUND ART

The yield in the semiconductor manufacturing front-end process is affected considerably by defects resulting from process abnormalities in various processes for wafer manufacturing and by circuit pattern defects stemming from process fluctuations.

Typically incurred defects include particles randomly produced and attached to the wafer and scratches caused by CMP. Also, there are pattern defects that occur only on the wafer edge as a result of the differences in manufacturing conditions between the wafer center and the waver edge in various processes (e.g., different plasma states in the etch process and differently heated states in the diffusion process).

Also, the representative process fluctuations that incur pattern defects include fluctuations of exposure conditions (in terms of focus and dose) under which circuit patterns are optically exposed in the lithography process. Such fluctuating factors can change the dimensions and shapes of circuit patterns, thereby possibly incurring faulty device properties.

In order to prevent the occurrence of such defects and to realize high-yield manufacturing, defect management and process management at the site of wafer manufacturing are becoming more and more important.

Wafer inspection tools are used for defect management. Traditionally utilized optical wafer inspection tools irradiate the wafer with illuminating light, detect reflected and scattered light from the wafer to image the wafer surface state, and inspect the wafer surface for detects through image processing. As such, the optical wafer inspection tool has throughput of about several to tens of minutes per wafer with detection sensitivity of 20 nanometers or larger. However, under defect detection conditions on the order of tens of nanometers, false alarms (not true defects) are often detected along with actual defects; it is difficult solely to detect true defects with high accuracy.

Meanwhile, SEM (Scanning Electron Microscope) type wafer inspection tools using an electron beam have been known to exist as an apparatus capable of inspection with higher sensitivity than optical wafer inspection tools. This type of apparatus images the state of the wafer surface by irradiating the wafer surface with a focused electron beam about a dozen to tens of nanometers in diameter and by detecting secondary electrons and the like emanating from the wafer surface. Although it has detection sensitivity of a dozen to several nanometers, this apparatus offers drastically lower throughput than optical wafer inspection tools. For this reason, the SEM type wafer inspection tool is often used in partial inspections covering only limited regions over the wafer. Patent Literature 1 and Patent Literature 2 cited below disclose methods for inspecting the wafer in part using an electron beam inspection tool. The disclosed methods involve performing defect inspection by limiting the area for inspection to partial regions such as memory mat peripherals of semiconductor memories.

Incidentally, defect review tools are used to observe and categorize the defects detected by these inspection tools. Since advances in process miniaturization have brought the size of defects affecting yield to smaller than tens of nanometers, electron beam type review tools (review SEM) are generally utilized. Defect position information obtained from the wafer inspection tool is taken as input, and an image of the region of interest is acquired with a resolution higher than at inspection time (e.g., a size of several nanometers per pixel) for identification and observation of types of defects.

Meanwhile, an example of process management is the monitoring of the lithography process using a CDSEM (Critical Dimension-SEM). The CDSEM is used periodically to measure the dimensions of the circuit patterns at predetermined positions on the wafer and to compare the measured dimension values with reference values for process management. Like the above-mentioned review SEM, the CDSEM is an apparatus that uses an electron beam and can acquire images with a resolution of about several nanometers. However, the number of positions that can be measured by this apparatus is limited because it takes as long as seconds to measure one position. For this reason, only predetermined positions are targeted for measurement. Technical Literature 3 cited below discloses a method for identifying the positions required for verification of a tolerable range of process fluctuations and for pattern measurement, using a wafer (e.g., FEM: Focus Exposure Matrix wafer) prepared by changing the exposure conditions for exposure process management into those applicable in units of chips. Incidentally, the FEM wafer is a wafer that has the same circuit pattern formed thereon with the focus and dose of exposure changed in a matrix pattern per die on the wafer. This wafer is subjected to the optical wafer inspection tool for inspection, which makes it possible to determine the location information about the positions where defects actually occurred and the focus and dose conditions that have prevented defects from being formed (the conditions are called the process window). Determined here as the positions to be measured are those that are likely expected to occur during process fluctuations such as defective positions on dies outside the process window.

PRIOR ART LITERATURE

Patent Literature

Patent Literature 1: JP-2010-67533-A (U.S. Patent 2011-0163230)
Patent Literature 2: JP-2011-119471-A
Patent Literature 3: U.S. Pat. No. 6,902,855

SUMMARY OF THE INVENTION

Problem to be Solved by the Invention

Patent Literature 1 shows examples in which the memory mat edge of a memory device known empirically as a position where defects are prone to occur is targeted for inspection with high sensitivity using an electron beam. However, advances in process miniaturization have entailed the introduction of new processes and the adoption of new materials, which can present the possibility that yet-to-be-known types of defects may occur at yet-to-be-known positions. According to the prior art, it is impossible efficiently to determine the regions to be inspected by means of electron beam inspection in such cases. That is, where empirical knowledge is insufficient, there is the problem of how to determine the regions to be inspected.

Also, Patent Literature 2 discloses a processing method for carrying out different items of inspection such as the determination of the presence or absence of defects and the measurement of pattern dimensions on partial regions using an SEM. Although this literature states that the regions where defects are found concentrated as a result of inspection by another inspection tool are to be set up as the regions to be partially inspected, there is no description of specific and detailed methods for implementing the proceedings.

Also, Patent Literature 3 shows a method for determining the positions to be measured for the dimensions necessary for the lithography process using a CDSEM, on the basis of not empirical knowledge but the result of optical wafer inspection on test-use wafers. However, as advances in process miniaturization have brought the amount of pattern fluctuations affecting the device to smaller than a dozen nanometers so that the testing sensitivity of optical wafer inspection tools turns out to be insufficient, the positions to be measured for dimensions by the CDSEM cannot be determined precisely according to the prior art. Although such infinitesimal defects are expected to be detected to a certain extent through optical wafer inspection under inspecting conditions with higher detection sensitivity (high-sensitivity mode) that would permit detection of defects on the order of a dozen nanometers, the above procedure can result in detecting a large number of false defects (false alarms detected by the inspection tool) in addition to true defects. This poses the problem of a heavy workload involved in isolating true defects from large quantities of defect candidates including the false defects.

Means for Solving the Problem

The present invention aims at efficiently determining the partial regions to be inspected with high sensitivity and measured with high accuracy.

According to an embodiment of the present invention, there is provided a region-of-interest determination apparatus including: a calculation unit which calculates the incidence of a defect based on at least a plurality of kinds of defect attribute information regarding defect data, the defect data including an image corresponding to a defect position detected on a specimen by inspection thereof or an image corresponding to a defect position predicted to be likely to develop a defect on the specimen, the images both being obtained by imaging; and a region determination unit which extracts the defect data of which the incidence is higher than a predetermined level, and determines the region to be observed or inspected on the specimen based on the extracted defect data.

According to another embodiment of the present invention, there is provided an observation apparatus or an inspection apparatus including: a calculation unit which calculates the incidence of a defect based on at least a plurality of kinds of defect attribute information regarding defect data, the defect data including an image corresponding to a defect position detected on a specimen by inspection thereof or an image corresponding to a defect position predicted to be likely to develop a defect on the specimen, both images being obtained by imaging; a region determination unit which extracts the defect data of which the incidence is higher than a predetermined level, and determines the region to be observed or inspected on the specimen based on the extracted defect data; and an image acquisition unit which acquires an image corresponding to the defect position based on information about the determined region.

According to a further embodiment of the present invention, there is provided a region-of-interest determination method including the steps of: calculating the incidence of a defect based on at least a plurality of kinds of defect attribute information regarding defect data, the defect data including an image corresponding to a defect position detected on a specimen by inspection thereof or an image corresponding to a defect position predicted to be likely to develop a defect on the specimen, both images being obtained by imaging; and extracting the defect data of which the incidence is higher than a predetermined level, and determining the region to be observed or inspected on the specimen based on the extracted defect data.

According to yet another embodiment of the present invention, there is provided an observation method or an inspection method including the step of determining the region on the specimen using the above-described region-of-interest determination method, and observing or inspecting the determined region.

Effect of the Invention

According to the present invention, it is possible efficiently to determine the partial regions to be measured for patterns and inspected for defects.

BRIEF DESCRIPTION OF THE DRAWINGS

FIG. 7 depicts a typical classified data display screen involved with the first embodiment.

MODE FOR CARRYING OUT THE INVENTION (First Embodiment)

Explained below as the first embodiment is a defect review system serving as an inspection tool that has functionality to inspect a specimen, i.e., more specifically to determine its regions to be inspected (measured) for patterns, using a CDSEM for process management in the lithography process.

Figure 1:
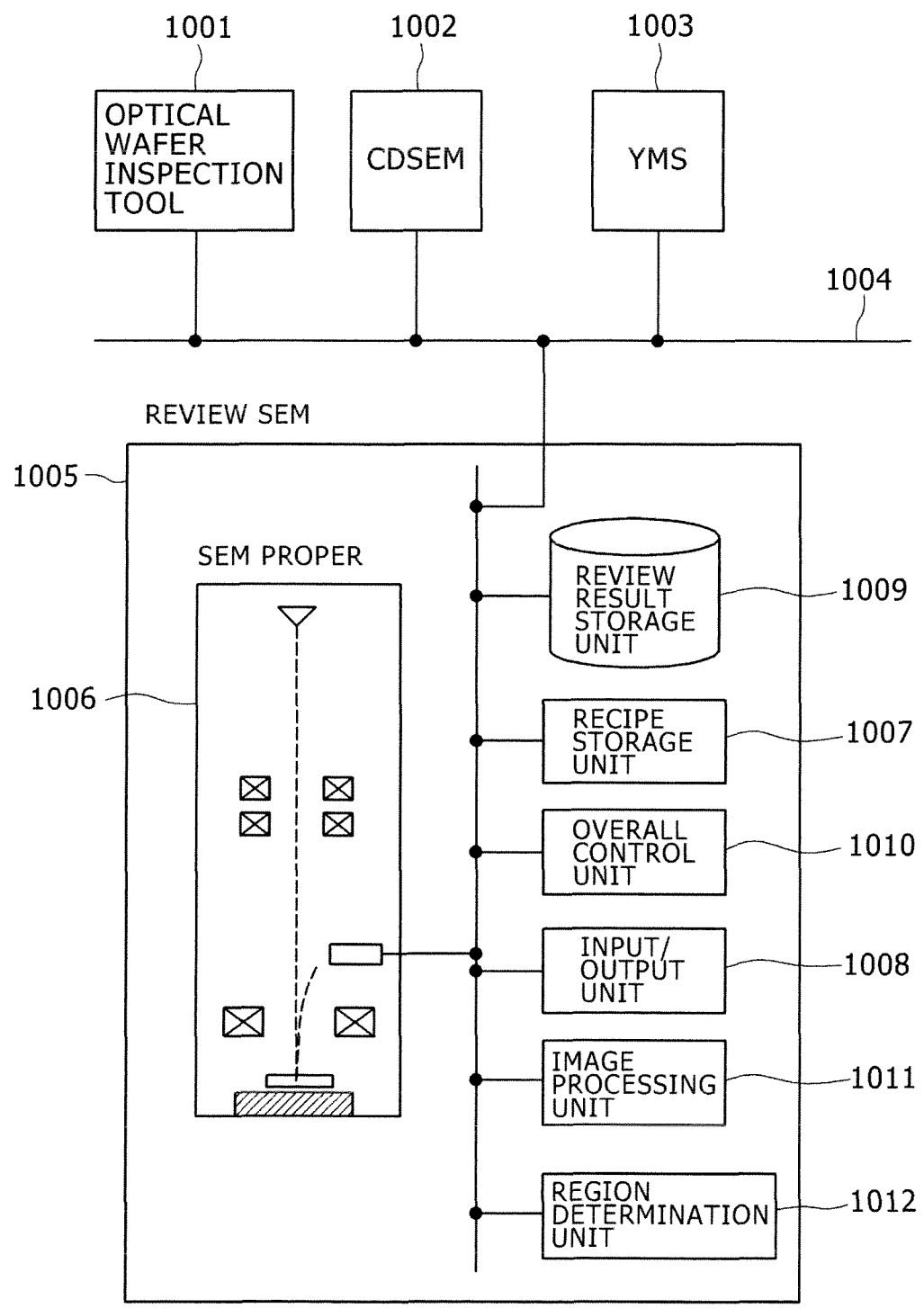
FIG. 1 is a general view of an inspection system involved with a first embodiment of the present invention.

FIG. 1 is a general view of an inspection system involved with the first embodiment. This is a general view of the inspection system that includes a review SEM 1005. An optical wafer inspection tool 1001, a CDSEM 1002, a yield management server (YMS) 1003, and the review SEM 1005 are interconnected via a network 1004. The major components constituting the review SEM 1005 include: an SEM proper 1006 that applies an electron beam to a wafer as a specimen mounted on a movable stage and performs a series of processes to acquire images; a recipe storage unit 1007 that stores the conditions for image acquisition (acceleration voltage for the electron beam to be applied, probe currents, the size of the field of view for imaging or imaging magnifications, addition of a plurality of frames to obtain better S/N ratios for image formation) and the recipes such as image processing parameters for defect detection; a review result storage unit 1009 that stores review results such as defect images taken and the coordinate values of the defects thus imaged; an input/output unit 1008 made up of a display device, a keyboard, etc., configured to be capable of input and output, of giving operating instructions to the review SEM 1005 and of displaying processing results therefrom; an overall control unit 1010 that controls the entire review SEM 1005 regarding a series of operations of the review SEM (reading of coordinate data, setting of imaging conditions from the recipe storage unit 1007 to the SEM proper 1006, acquisition of images, storage of acquired images into the review result storage unit 1009, image processing, etc.); an image processing unit 1011 that performs image processing such as the recognition of defects from acquired images; and a region determination unit 1012 that determines the regions to be measured (regions to be inspected) based on the review results. The SEM 1006, recipe storage unit 1007, input/output unit 1008, review result storage unit 1009, overall control unit 1010, image processing unit 1011, and region determination unit 1012 are interconnected electrically. Incidentally, the SEM proper 1006 functions at least as an image acquisition unit.

Figure 2:
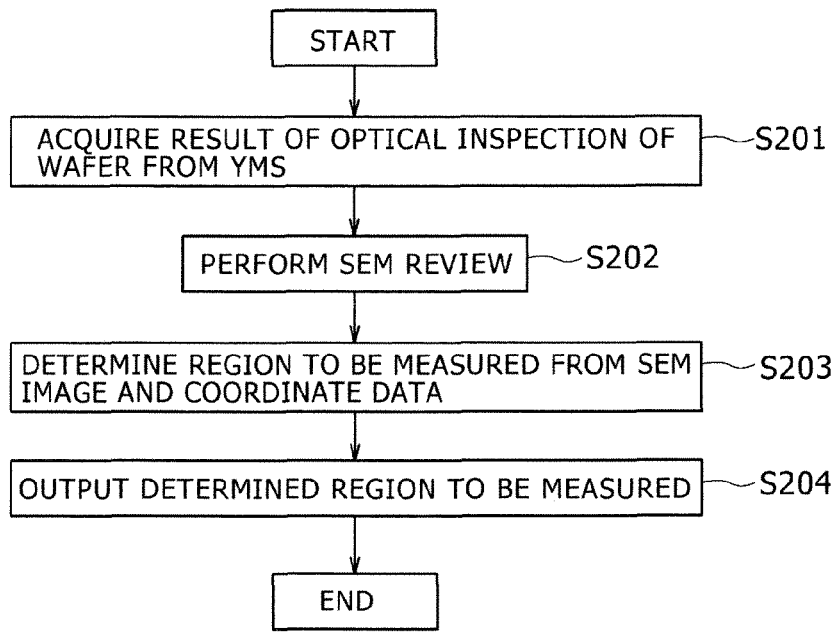
FIG. 2 depicts a process flow of the first embodiment.

FIG. 2 depicts a process flow of a series of steps performed by this system. It is assumed here that prior to the process, the inspection of an FEM wafer performed using the optical wafer inspection tool 1001 is completed and that the result of the inspection has been stored in the YMS 1003. First, the inspection result is retrieved from the YMS 1003 by the review SEM 1005 before being stored or written to the review result storage unit 1009 (S201). Next, the result is reviewed using the review SEM 1005 (S202). The review involves getting the review SEM 1005 to acquire a SEM image corresponding to the position of each defect based on the information of the inspection result acquired from the YMS 1003 regarding the FEM wafer of interest. More specifically, the review involves performing a sequence of steps for acquiring an image by moving the stage carrying the specimen wafer in such a manner that the coordinates of a defect on the wafer come into the field of view for imaging, the sequence being repeated while the target defect is changed one after another. Through this review, chip ID numbers (for uniquely identifying each of a plurality of chips on the wafer), coordinate positions inside each chip, and a SEM image corresponding to each of the positions are acquired as a single set.

To acquire an image requires setting the size of the field of view to about several micrometers in order to analyze defects in detail either visually or through image processing. Meanwhile, the coordinates of a defect output by the optical wafer inspection tool 1001 are known to include a positional error. When the amount of the error is several micrometers, the defect of interest may not come into the field of view if the image is acquired with the field of view set to several micrometers in size. In such cases where the wafer inspection tool has a large error, it may be preferable to perform a sequence that includes first acquiring an image under the condition of the field of view being extended to, say, a dozen micrometers, then acquiring the defect automatically from the image through processing by the image processing unit 1011, and finally obtaining an image corresponding to the defect position thus detected using the field of view set to several micrometers that are smaller than the size of the field of view used earlier. Performing the above sequence will make it possible efficiently to detect defects.

When the process is to be carried out automatically to detect the position of a defect from an image with a wide field of view, it may be advisable to obtain beforehand a reference image regarding the position in question in addition to the image corresponding to the defect position so as to compare the two images by what is known as the comparative inspection method. The reference image is obtained by imaging a normal chip different from the chip containing the defect of interest, the defect-free chip having the coordinates of the detect which are the same as those on the defect-carrying chip and which are targeted for image acquisition. The chip for reference image acquisition may be located beforehand when spotted and designated for its relatively good exposure conditions.

Incidentally, if the wafer is optically inspected through comparison with reference chips, the position of a comparative chip (usually, one of a plurality of chips contiguous with the chip to be inspected) used in the inspection may be registered.

After the processing above, a chip ID number (for uniquely identifying the chip of interest on the wafer) as position coordinate information on defect candidates, the coordinate position inside the chip, and a SEM image corresponding to that position are acquired as one set.

Where the optical wafer inspection tool 1001 is used to inspect the wafer, the inspection is often carried out under high-sensitivity conditions so as to detect infinitesimal shape defects, such as shape anomalies of tens of nanometers in size. This means that the inspection result is highly likely to contain large quantities of false defects (i.e., noise data other than defects) in addition to true defects. In such a case, it would be inefficient to inspect the total number of defects output by the optical wafer inspection tool 1001. Instead, a SEM review should preferably be conducted only on the partial defect data sampled by some appropriate method.

Next, the region determination unit 1012 determines the region to be measured (region to be inspected) using the above data (S203).

Figure 3:
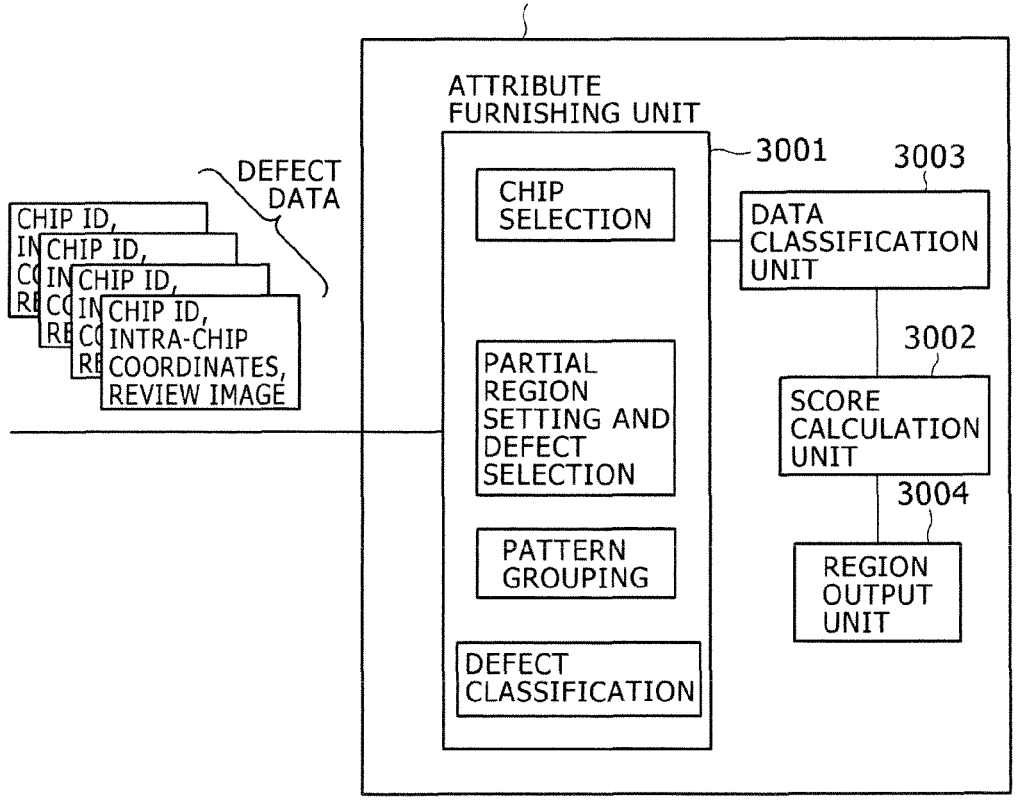
FIG. 3 is an internal block diagram of a region determination unit involved with the first embodiment.

FIG. 3 is an internal block diagram of the region determination unit 1012. The defect data to be input is a set composed of a chip ID, intra-chip coordinates, and a review image of each defect. There exist as many sets of such data as the number of defects targeted for processing.

Included in the region determination unit 1012 are an attribute furnishing unit 3001 that furnishes diverse attribute information (to be explained later) to each set of defect data, a data classification unit 3003 that classifies defect data based on the attribute information, a score calculation unit 3002 that calculates evaluation scores of classified data and furnishes the calculated scores to the data, and a region output unit 3004 that determines the region to be measured for patterns (region to be inspected) based on the diverse information and outputs the region thus determined. The score calculation unit 3002 functions, it may be noted, at least as a calculation unit that calculates an evaluation score of a defect as the incidence thereof based on at least a plurality of kinds of attribute information of the defect data including an image corresponding to a defect position detected on a specimen by inspection thereof or an image covering the defect position predicted to be likely to contain or develop that defect on the inspected specimen.

Also, the region output unit 3004 functions at least as a region determination unit which extracts defect data of which the above-mentioned incidence is higher than a predetermined level and which determines the region over the specimen to be observed or inspected based on the extracted defect data.

Figure 4:
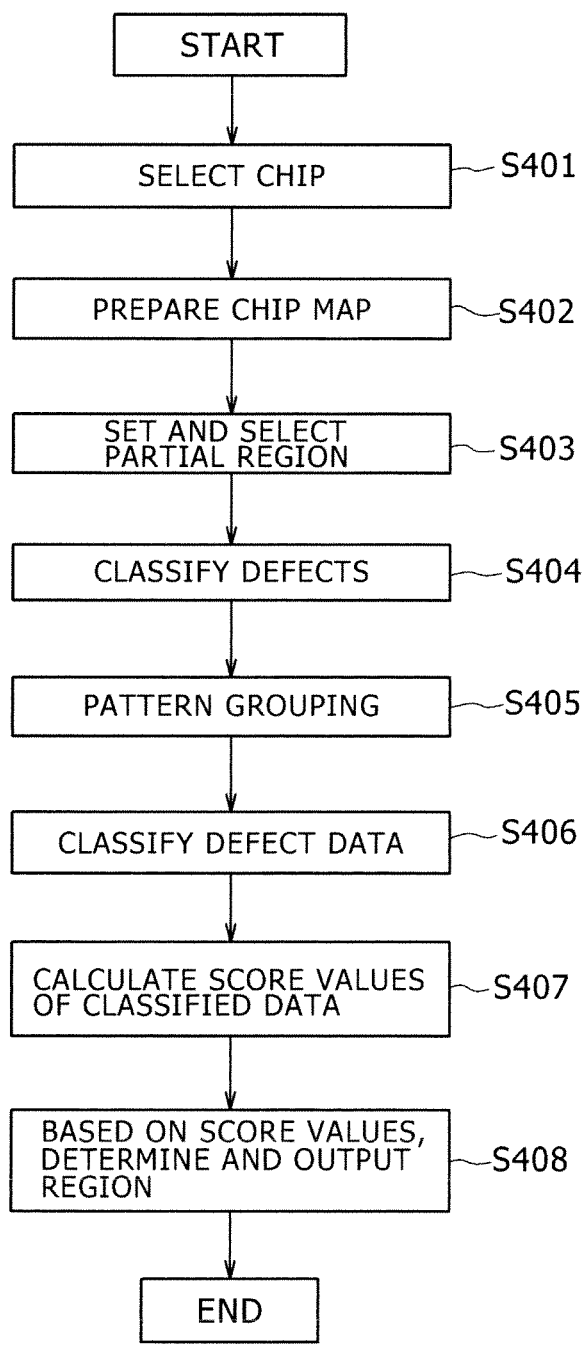
FIG. 4 depicts a region determination process flow of the first embodiment.

FIG. 4 depicts a process flow of the region determination unit 1012. The purpose of this process is to have a defect data set input as a plurality of kinds of defect attribute information, analyze the information for shapes and positions that are likely to develop defects, and determine the regions to be measured for patterns (inspected for patterns on the specimen) with the CDSEM 1001 based on the result of the analysis. For that purpose, the attribute furnishing unit 3001 sets a plurality of types or kinds of attribute information (or attribute values) for each set of defect data. First, evaluation target chips for use in the subsequent processing are automatically selected from among all chips on the wafer (S401). Each defect data set is furnished with attribute information as to whether the defect in question exists on the selected chips. The chips targeted for the subsequent processing are selected by examining the number of defects on each of the chips identified by the chip IDs furnished to the defect data and by isolating the chips of which the number of defects falls within a predetermined range. This chip selecting process makes it possible to exclude from the subsequent processing the chips of which the number of defects exceeds the predetermined range and those of which the number of defects falls short of the predetermined range for example.

Figure 5A:
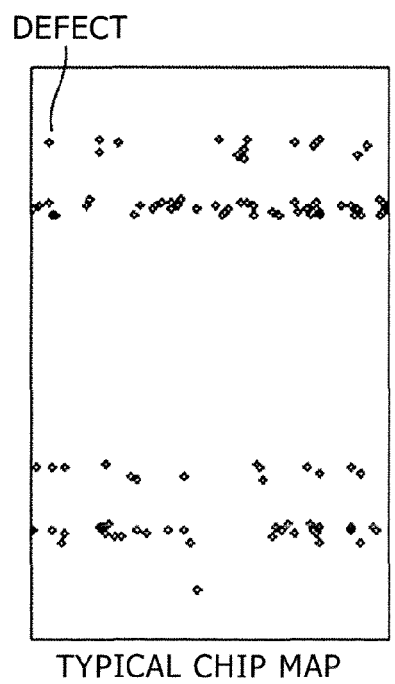
FIG. 5A is a typical chip map of the first embodiment.

Next, a chip map is prepared in which the intra-chip coordinate position of each of the defects included in the process target chips is plotted on a single chip layout (S402). FIG. 5A depicts a typical chip map. It displays the plotted positions where defects exist on the chips. The chip map makes it possible to visualize the difference in defect concentration between different positions inside the chips.

Figure 5B:
FIG. 5B depicts an example in which partial regions are set in the chip layout of the first embodiment and an example in which those partial regions whose defect concentration is high are selected.

Partial regions are set on that chip map and, from among the partial regions thus established, those of which the defect concentration exceeds or falls within a predetermined range are selected (S403). The partial regions are set and the inspection target regions are selected by dividing the chip layout into a plurality of rectangular regions and by selecting those rectangular regions in which the number of defects exceeds a predetermined threshold value, for the purpose of identifying the positions where defect concentration is high (i.e., locations likely to develop defects). FIG. 5B shows an example in which partial regions are set in the chip layout and an example in which partial regions whose defect concentration is high are selected. The partial regions are indicated by dotted lines (9×6=54 regions). Of these regions, 11 regions are shown selected (indicated by thick lines). The defects are each furnished with attribute information indicating whether the defect in question exists inside the established partial regions. Then the defects included in the selected partial regions are targeted for a defect classification process whereby the defects are furnished with attribute information regarding defect types (S404). The defect classification process involves subjecting SEM images to image processing so as to classify the SEM images into different defect types. For example, the process may be carried out using the automatic defect classification function (ADC) currently incorporated in the standard review SEM. This is a function that automatically classifies SEM images into different defect types by performing image processing on the SEM images. In this context, the defect types refer to such classified defects as attached foreign matter, pattern-short, and pattern-open.

Carried out next as a sort of the process of furnishing defect attribute information is a pattern grouping process that takes note of reference patterns regarding the defects included in the selected partial regions (S405). This process takes note of the fact that patterns similar to each other in shape are highly likely to develop similar kinds of defects (e.g., pattern-short and pattern-open). As such, the process involves grouping together, from an aggregate of process target defect data, those defects of which the circuit pattern characteristics (pattern width, distances to the adjacent patterns, layout, etc.) are similar to one another.

The grouping process is performed as follows:

It is assumed that reference image data was obtained along with the image data of the defect positions upon execution of a SEM review on each defect (S202). With regard to the reference image data, the cross-correlation coefficient method is used to obtain quantitative values indicative of how similar the image data are to one another. Then the defects of which the similarities are higher than a predetermined level are considered to form the same group.

Figure 6A:
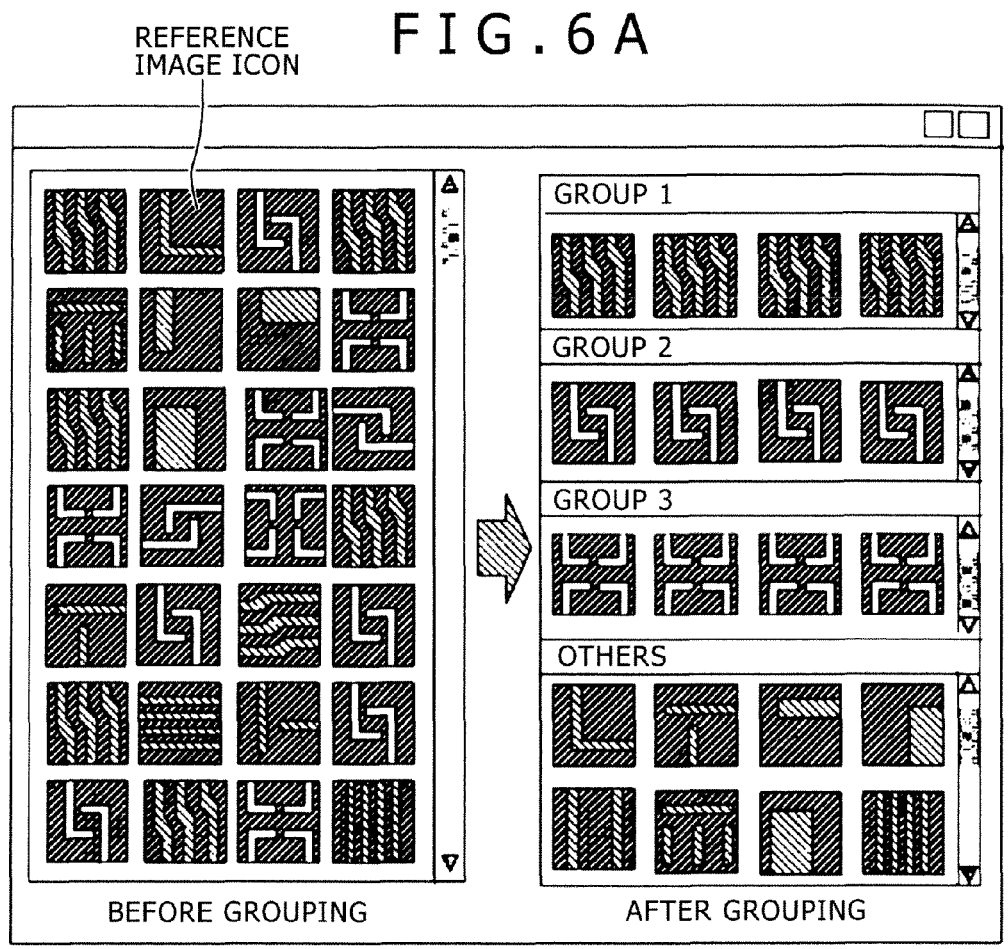
FIG. 6A depicts a typical display screen showing the result of pattern grouping involved with the first embodiment.

FIG. 6A depicts a typical display screen that shows the result of pattern grouping involved with the first embodiment, illustrating schematically the effect of the process. This is an example that depicts both grouped icon images and yet-to-be-grouped icon images representing the defect data included in the partial regions shown selected in FIG. 5B. In this example, there are three patterns (groups 1, 2 and 3) of similar images. By means of the grouping process, the image data is rearranged into groups of similar patterns. Incidentally, the group indicated as "others" on the display of the grouping result in FIG. 6A is an aggregate of cases in which no other image was found similar to the pattern in question.

When images are to be evaluated for similarities, it is possible to compare an aggregate of images with numerous images prepared by such geometrical transformations as rotation, enlarging and contraction. Preferably, not all regions of images but partial regions therein may be compared for similarities. For example, given the data of each defect, the image corresponding to the defect position may be compared with the corresponding reference image (so as to calculate a difference image). This makes it possible to identify the position where a given defect exists inside the images and to compare only the partial image regions including the identified defect position for similarities. This provides the effect of shortening processing time because the regions used for similarity calculations are limited.

Figure 6B:
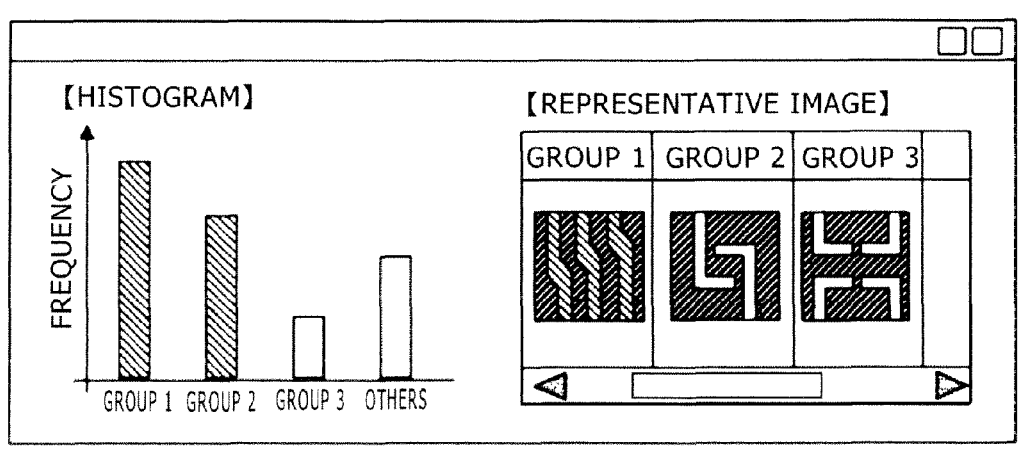
FIG. 6B depicts another typical display screen showing the result of pattern grouping involved with the first embodiment.

FIG. 6B depicts another typical display screen showing the result of pattern grouping involved with the first embodiment. In this example, the frequencies of the groups involved are graphically indicated for visualization purposes. Specifically, the result of the grouping is displayed as a histogram. Alternatively, the histogram may be replaced with a pie chart or a line graph. Preferably, as shown in FIG. 6B, representative images of the groups involved may be displayed on the same screen. This allows the images representing the groups found in the graph to be visually recognized with ease.

As another example of the result of pattern grouping, a chip map such as one shown in FIG. 5A may preferably be prepared by designating any one of the groups acquired from the grouping and by using the defect data included in the designated group. This makes it possible to verify where a given pattern having a particular shape is located on the chips. These display screens appear on the input/output unit 1008 of the review SEM 1005 and are easily verified by the tool operator. As a result of the pattern grouping process, each defect is furnished with the attribute information as to which group the defect in question belongs to.

The foregoing paragraphs outlined the process of furnishing diverse attribute information to defect data. Specifically, the attribute information was shown furnished in terms of whether the defect in question is included in the selected chips, whether the defect is included in the partial regions set up inside the chip layout, what type of defect the defect data in question represents, and which group the defect is determined to belong to through the pattern grouping process.

Next, based on the attribute information thus obtained, the data classification unit 3003 classifies the defect data (S406). FIG. 7 shows an example in which the result of data classification based on the attribute information furnished to each defect is displayed on the input/output unit 1008. What is shown here is the result of classifying the input set of defect data in terms of whether the defect is included in the selected chips and whether the defect is included in the selected partial regions, the result of automatic classification (defect type), and the result of pattern grouping. Furthermore, the result of the grouping is displayed along with representative examples of the groups involved. Shown in the lower part of FIG. 7 are a chip layout and selected chips on the wafer, as well as a defective chip map and the partial regions established.

Then the selected data groups are each furnished with a score value calculated by the score calculation unit 3002 (S407). The score value is a value for calculating the incidence of defects and is given to the data group in question as an indicator of its degree of importance in terms of yield management and process management. FIG. 7 also shows the score value furnished to each of the classified defect groups. A score value is obtained as follows: a unit score value is defined beforehand for each of the criteria for data classification. The product is then calculated of the unit score values defined individually for all criteria used to acquire the ultimate result of the classification. For example, it may be assumed that the unit score regarding chip selection is defined to be 10 for selected data and 0 for unselected data; that the unit score regarding the criterion for partial regions is defined to be 10 for intra-region data and 0 for out-of-region data; that the unit score regarding the result of defect classification is defined to be 10 for shape defects such as pattern-short and pattern-open and 5 for other defects such as foreign matter; and that the unit score regarding the result of pattern grouping is defined to be 10 for the groups other than the group "others" and 5 for the group "others." In this case, a pattern shape defect which exits inside the selected chips and inside the partial regions and which is determined to belong to group 1, for example, as a result of pattern grouping is given a score value of 10,000 (10×10×10×10).

Alternatively, the score value may be defined as follows: Suitable criteria are selected as needed and a unit score value is defined for each of the selected criteria so that the product of the unit score values defined for the selected criteria may be calculated. This eliminates the need for defining beforehand the unit score value for each of the criteria for data classification and calculating the product of the unit score values defined individually for all criteria used to acquire the ultimate result of the classification.

Explained so far was one embodiment of the process of data classification based on the diverse attribute information furnished to the defect data and of furnishing score values to the defect of interest. However, this embodiment is not limitative of the present invention when it is embodied. Alternatively, not all but some of the above-mentioned kinds of attribute information may be utilized. As other examples of the way in which attribute information is furnished to each defect, there may be a method of furnishing the information based on whether or not the dimensions of each defect fall within a predetermined range, and a method of furnishing the attribute information based on how each defect overlaps with background patterns (e.g., over the substrate, over the boundary between the circuit pattern and the substrate, or over the patterns).

In the foregoing paragraphs, there was explained the process of calculating the ultimate score value using unit score values based on the attribute information acquired from each defect candidate. As explained above, a plurality of unit score values are defined. When the incidence of defects is calculated on the basis of multiple kinds of defect attribute information, an important defect of interest is efficiently identified from numerous and diverse defect candidates, and the regions to be inspected are determined accordingly.

At the stage of process development, a large number of defect candidates occur. These candidates are a mixture of defects attributable to a plurality of factors including the materials used and the manufacturing conditions of production equipment in addition to pattern designs such as circuit pattern shapes. As process development advances, the type of the defect to be noted at a given point in time varies. Thus when the incidence of defects is calculated based on a plurality of kinds of defect attribute information, it is easy to deal with the defects of varying importance that occur in keeping with the maturity of the process.

In particular, the attribute information related to the most important unit score values according to this invention is the information about the result of pattern grouping. Preferably, the information about the result of pattern grouping should at least be included in the above-described multiple kinds of defect attribute information used as the basis for calculating the above-mentioned incidence of defects. That is because the circuit pattern shapes at or near the positions of defect candidates become important as the lithography process is getting increasingly miniaturized.

The information regarding the result of pattern grouping is particularly effective in classifying the defect candidates attributable to circuit pattern designs.

The pattern grouping process is accomplished using images of defect candidate points acquired by a high-resolution SEM.

Also, the classification information about defect types is important in efficiently classifying the defect candidate from among numerous defects. Preferably, the information about defect types should preferably be included in the above-mentioned multiple kinds of defect attribute information used as the basis for calculating the above-described incidence of defects.

In this manner, it is possible to exclude from the targets for evaluation those defects of surface foreign matters which occur randomly and which may be found mixed in pattern shape defects frequently occurring during the lithography process. Also, it may or may not be possible to handle by the same method the pattern shape defects of various types including pattern-short, pattern-open, or dwindling or thickening patterns about to become defects. Thus classifying the defects using the attribute information about defect types contributes to making subsequent processing more efficient.

Furthermore, the chip position information about defects on the specimen and the information about the defect positions inside the chips are also important in efficiently classifying defect candidates from among numerous defects. Preferably, the information about defect types should preferably be included in the above-mentioned multiple kinds of defect attribute information used as the basis for calculating the above-described incidence of defects.

If in-plane uniformity cannot be maintained in the manufacturing process, the degree of defect incidence varies depending on the position over the wafer, such as on the edge of the wafer on the one hand and at the wafer center on the other hand. Thus when the defect position information is included in the attributes, it is possible efficiently to classify the defects incurred inside the wafer surface as a result of variations in the manufacturing process. Inside the chips, the positions where patterns concentrate and those where pattern concentration is low usually exist in mixed fashion, and the defect type varies from one region to another. For this reason, depending on the defect type of interest, it is also effective to classify the defect candidates in terms of pattern concentration.

In carrying out the present invention, it is possible obviously to classify defect candidates by using only the attribute information related to the above-mentioned important unit score values while disregarding the other unit score values of lesser importance.

Next, the regions to be measured (regions to be inspected) are determined based on the score values before being output (S408). That is, the defect data of which the score value as a defect incidence is higher than a predetermined value is extracted, and the regions to be inspected on the specimen are determined from the defect data thus extracted.

Because the purpose here is to determine the positions to be measured (positions to be inspected) by the CDSEM 1002 and to output the determined positions, the output data is constituted by the coordinate values of the positions to be measured as the regions to be inspected. For that purpose, a group of data having score values higher than the predetermined values is selected from the result of data classification, and the coordinate values of the defect data included in that data group are output. Since the defect positions included in each data group may or may not be the same in the chip layout, the coordinate values are next subjected to a clustering process. The clustering process is a process in which, given the data from various results of classification, the data with their intra-chip coordinate values falling within a predetermined tolerance (e.g., ±100 nm) are regarded as data about the same position (as one cluster). Thereafter, an average of the coordinates of the data included in each cluster is calculated.

It should be noted that the coordinate data is composed of coordinate values obtained from the wafer inspection tool, so that the data contains measurement errors stemming from the time of wafer inspection. For this reason, even if the CDSEM 1002 is used to observe the determined coordinates of a given position, that position may be different from the desired position to be measured. One way of solving this problem is by outputting to the YMS 1003 a circuit pattern image (e.g., representative image obtained as a result of the grouping process) along with the coordinate data of the position to be measured and by getting the CDSEM 1002 to use both the circuit pattern image and the coordinate data. The pattern image acquired along with the coordinates of the point to be measured is stored inside the CDSEM 1002. At the time of acquiring images of each point to be measured, an image with a wide field of view including the measurement point coordinate position is first obtained. Then from that image, the position where the pattern image exists is obtained through a pattern matching process. Thereafter, an image corresponding to the position of the identified circuit pattern is obtained anew as an image for measurement. This image is then subjected to the measuring process.

Another way of solving the above problem is by acquiring the coordinate values on a CAD layout via a system that matches SEM image data against CAD layout data. This technique may be implemented using a setup shown in FIG. 8 for example. The setup in FIG. 8 differs from that in FIG. 1 in that a layout analysis unit 1014 is connected to the region determination unit 1012. The layout analysis unit 1014 is further connected to layout CAD data 1015.

Figure 8:
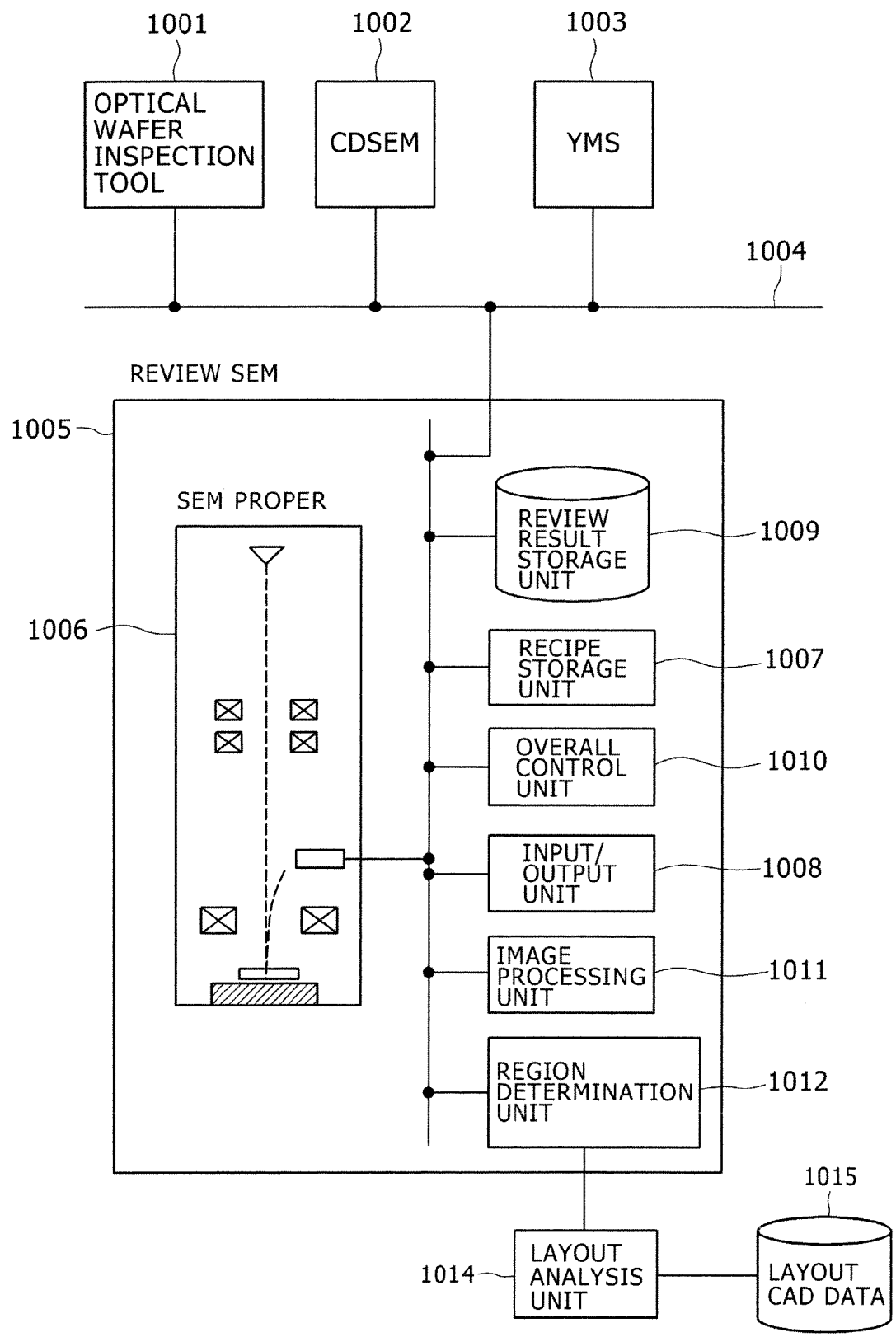
FIG. 8 is a general view of another inspection system involved with the first embodiment.
Figure 9:
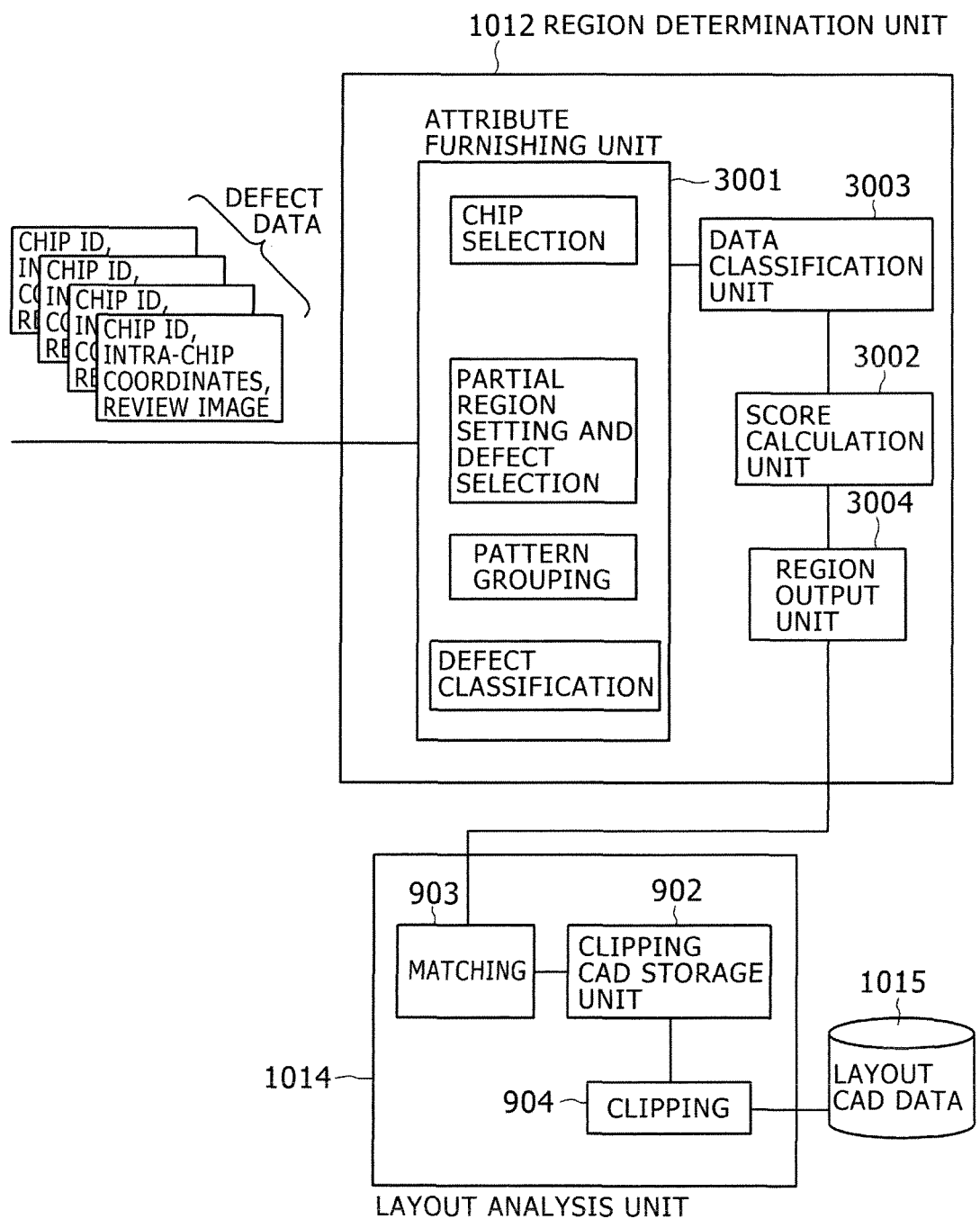
FIG. 9 is a block diagram of a region determination unit in the inspection system shown in FIG. 8.

FIG. 9 is a block diagram of the region determination unit 1012 in the setup depicted in FIG. 8. The block diagram in FIG. 9 differs from the block diagram of the region determination unit 1012 shown in FIG. 3 in that the layout analysis unit 1014 is connected to the region output unit 3004 and that the layout analysis unit 1014 is further connected to the layout CAD data 1015. The inside of the layout analysis unit 1014 is constituted by a clipping unit 904 that extracts (clips) the local CAD data of a desired position from the layout CAD data 1015, a clipping CAD storage unit 902 that stores clipping data from the clipping unit 904, and a matching unit 903 that matches the stored clipping data against SEM images.

The layout analysis unit 1014 receives the coordinate data of the position for measurement determined by the region output unit 3004 along with a SEM image corresponding to that position, and stores what is received into the matching unit 903. The layout analysis unit 1014 then reads the design layout data of the circuit pattern from the layout CAD data 1015, causes the clipping unit 904 to clip a CAD data image of a region sufficiently wider than the field-of-view size of the SEM image corresponding to the position in question, and stores the clipped image into the clipping CAD storage unit 902. Thereafter, the layout analysis unit 1014 causes the matching unit 903 to match the acquired clipping data against the SEM image in a pattern matching process to recognize the position in the clipping data which matches the position of which the SEM image was obtained. Thus, CAD layout data coordinate values of the position to be measured can be obtained. This method makes it possible to acquire error-free coordinate data. Incidentally, this method may be carried out before the above-described clustering process involving coordinates.

The coordinate values or the pattern images thus obtained of the positions to be measured are output to and stored into the YMS 1003 (S204). The coordinate information about these points to be measured can be used in evaluating process conditions and design circuit patterns during process development work.

Since the coordinate values determined as described above are intra-chip coordinates, actual measurement of the wafer requires designating the chips to be measured and the intra-wafer coordinates of these chips. For example, if it is desired to again obtain an image of the FEM wafer that was used for determining the points to be measured, the next chip targeted for measurement is designated, and the intra-wafer coordinates of the origin of that chip are obtained along with the intra-chip coordinates of the obtained points for measurement, whereby the position to be measured can be calculated in a wafer coordinate system.

The points for measurement thus output may also be used as production monitoring positions for mass-producing the device in question. That is, the positions determined to be prone to develop defects as a result of the inspection at the stage of process development may be registered in the YMS 1003 so that at the stage of mass production, these positions can be measured.

(Second Embodiment)

In connection with the first embodiment, the example was shown above in which the regions to be measured are extracted from the defect candidates detected by the wafer inspection tool regarding the lithography process. In the lithography process, the patterns to be observed are usually formed by a resist layer (single layer resist). Also, the major defects are shape defects such as pattern-open, pattern-short, dwindling or thickening patterns. The incidence trend of these defects is closely associated with the local shapes of the circuit pattern. In connection with the second embodiment, an example will be explained hereunder in which the regions to be inspected are determined as inspection position identification information regarding the inspection of the wafer performed following completion of the other process, for example, the etch process of various patterns. In this case, the assumption is that the defect types to be targeted include not only shape defects but also diverse process-related defects. When defect management is conducted on process wafers having a multilayer structure following completion of the etch process, it is generally difficult to utilize test wafers such as the FEM wafer used in the lithography process because of the numerous factors that can affect the incidence of defects. Therefore, test circuit patterns and actual circuit patterns are fabricated in the actual manufacturing process; these patterns are then subjected to wafer inspection to identify defect positions; and the partial regions to be inspected are extracted from the data thus obtained.

Figure 10:
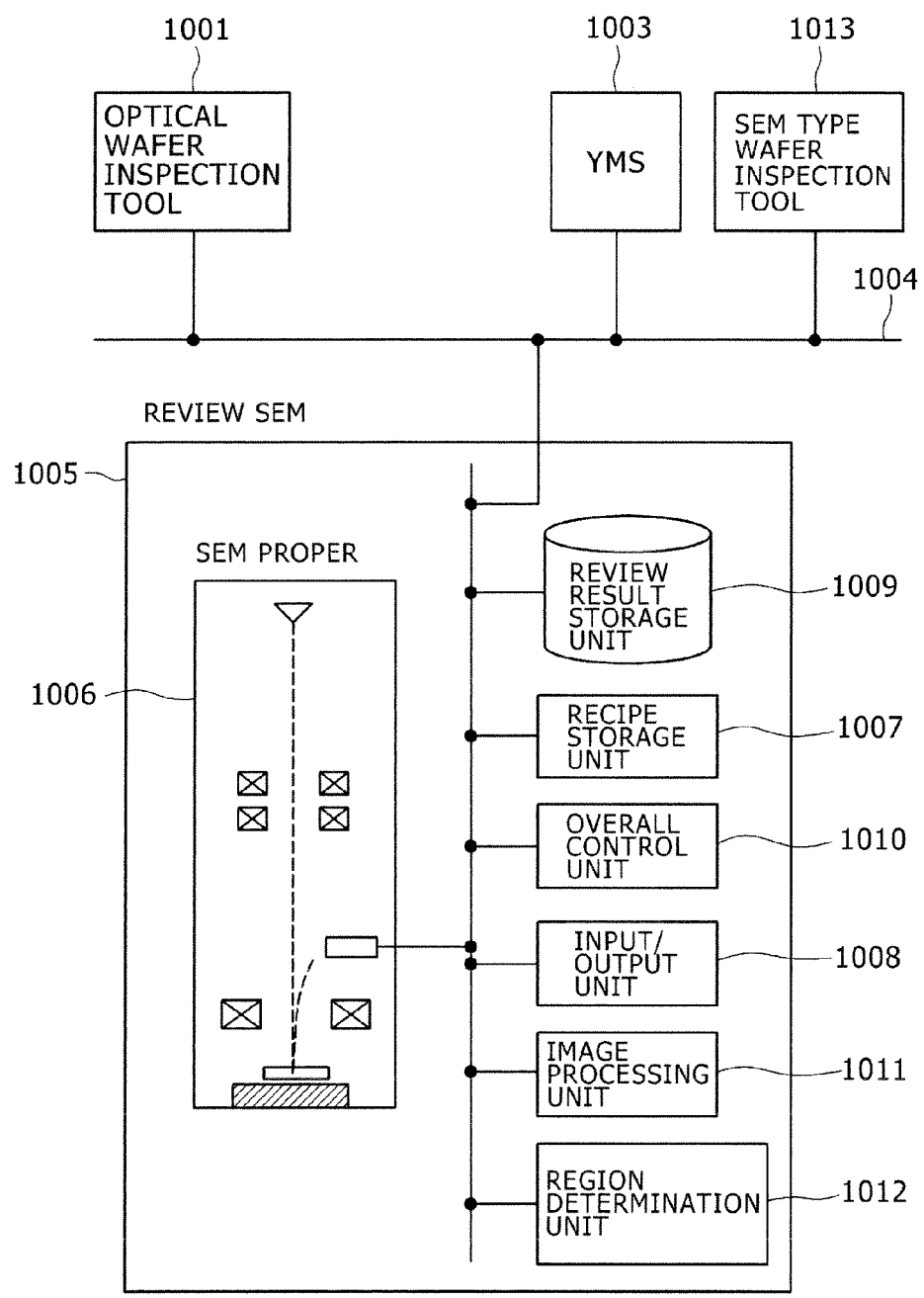
FIG. 10 is a general view of an inspection system involved with a second embodiment of the present invention.

FIG. 10 is a block diagram of the inspection system involved with the second embodiment. This system differs from the system explained above in connection with the first embodiment (FIG. 1) in that a SEM type wafer inspection tool 1013 is connected to the network 1004. The process flow of the second embodiment for determining the regions to be inspected as the inspection position identification information is approximately the same as the process flow of the first embodiment, i.e., about the same as depicted in FIG. 2.

As shown in FIG. 2, the result of the inspection performed by the optical wafer inspection tool 1001 on an actual process wafer for evaluation use is first obtained from the YMS 1003 (S201), and a SEM review is carried out (S202). As with the first embodiment, the second embodiment acquires reference images that match the images corresponding to defect positions during the SEM review. The reference chips from which to obtain the reference images are those contiguous with the chips containing the defects. Next, the regions to be inspected are set as the inspection position identification information using the IDs of the chips containing the defects, intra-chip coordinate values, and the acquired images (S203). Although the flow of this process is basically the same as the flow in FIG. 4 explained above in conjunction with the first embodiment, there are some details that differ between the two embodiments. These detailed differences will be mainly explained below.

Figure 11:
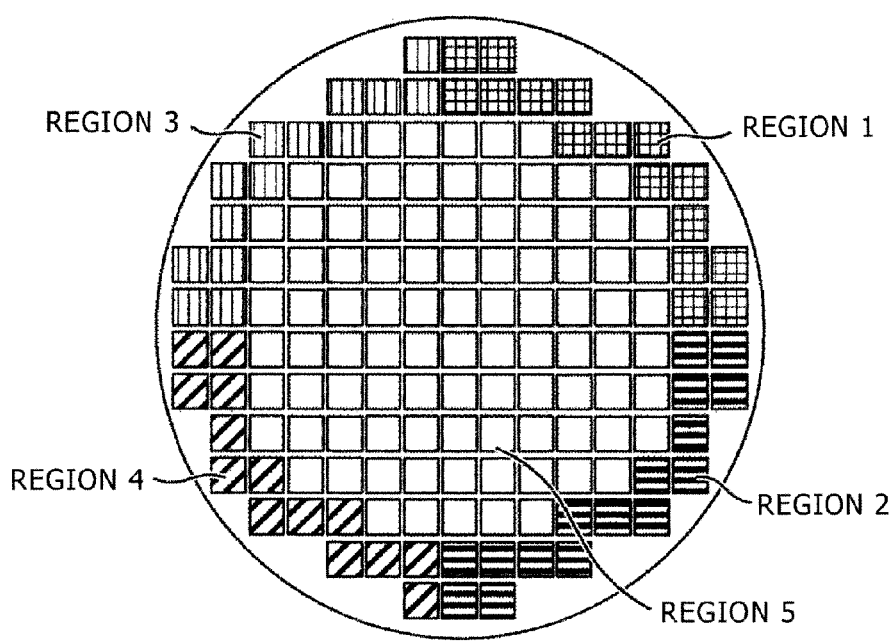
FIG. 11 is an explanatory drawing of wafer region division involved with the second embodiment.

Chips are first selected from the wafer divided regions (S401). With the first embodiment, evaluation data was classified on a chip-by-chip basis. That was because the process conditions differ from one chip to another on the FEM wafer. With the second embodiment, by contrast, chips are selected by taking into account their overall positions on the wafer. That is, the wafer is divided in the diametrical and circumferential directions into a plurality of regions, and the chips are selected from each of the divided regions. This takes note of the fact that the incidence trend of defects likely varies depending on the position over the wafer (e.g., distance to the wafer edge). FIG. 11 shows an example in which the chips on the wafer are divided into five regions, four of which are from groups of chips on the wafer circumference being directionally divided, the remaining one region being a group of chips other than those on the wafer circumference. The groups of chips on the wafer circumference are directionally divided into region 1 shown in a lattice pattern, region 2 in a horizontal stripe pattern, region 3 in a vertical stripe pattern, and region 4 in a diagonal stripe pattern, in contrast with region 5 as the group of chips shown blank other than the chips on the wafer circumference. A desired number of chips are selected from each of these divided regions.

Figure 12A:
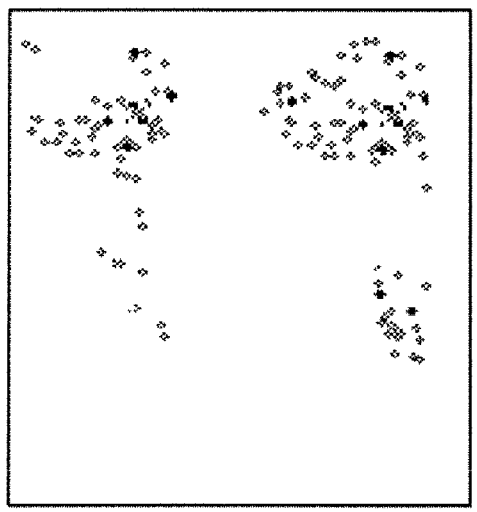
FIG. 12A is a typical chip map prepared from region 1 shown in FIG. 11 in connection with the second embodiment.
Figure 12B:
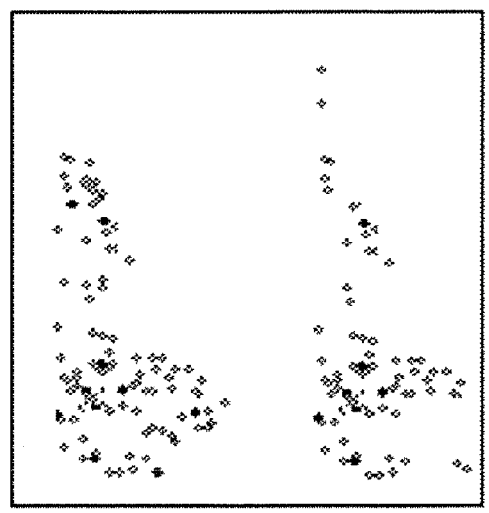
FIG. 12B is a typical chip map prepared from region 4 shown in FIG. 11 in connection with the second embodiment.

Next, attributes are furnished to the defect data included in the selected chips. Initially, as with the first embodiment, a chip map is prepared of the process target chips as a first attribute (S402). The partial regions where defect concentration is high are identified (S403). The chip map is prepared of each of the divided regions on the wafer shown in FIG. 11. FIGS. 12A and 12B depict a chip map each. FIG. 12A shows a typical chip map prepared of region 1 in FIG. 11 (the top right chip group on the wafer circumference), and FIG. 12B gives a typical chip map prepared of region 4 in FIG. 11 (the bottom left chip group on the wafer circumference). It can be seen how the positions of high defect concentration differ between region 1 and region 4. This example shows that defect concentration is elevated in the regions near the outer circumference of the wafer. The partial regions are set in the same manner as explained above in conjunction with the first embodiment with reference to FIGS. 5A and 5B.

Next, a class attribute (attribute information) of the defect type obtained using the ADC (automatic defect classification function) is furnished (S404). Furthermore, the grouping process is carried out using reference images (S405). The purpose of the grouping process with this embodiment is to distinguish, say, the circuit patterns called dummy patterns whose electrical characteristics are meaningless from the other circuit patterns. The dummy patterns may be located anywhere on the chip, and are frequently different from the characteristic and normal circuit pattern shapes such as a square pattern. Also, the characteristic patterns are noted for the ease of recognition through the pattern grouping process. Because the defects on the dummy patterns have no effect on yield, these defects can be excluded from the target for processing.

Next, based on the attribute information obtained so far, the defect data is classified (S406), and a score is furnished to each defect data group (S407). The classification and the furnishing of the scores are carried out in the same manner as explained above in conjunction with the first embodiment.

Figure 13:
FIG. 13 is a typical classified data display screen involved with the second embodiment.

FIG. 13 shows a typical screen displaying the result of the classification on the input/output unit 1008. Because the chips are selected from each of the regions obtained by dividing the wafer layout as shown in FIG. 11, the classification result is shown divided regarding each of the regions involved (regions 1 to 5 in this example; only the result of region 1 is shown in FIG. 13). The example shown in FIG. 13 indicates that there are 225 defects found on the chips selected in region 1 on the wafer, the defects being included in the partial regions defined based on defect concentration. Of these defects, 200 are foreign matter defects and 25 are other defects. Of the 200 foreign matter defects, 165 are found belonging to group 1 of dummy patterns as a result of pattern grouping and the other 35 are found in the background patterns.

Then based on the score values, the regions to be inspected are determined as inspection position identification information that is output (S408). With the first embodiment, what was determined were the positions to be measured. With the second embodiment, the regions each having a predetermined area are determined as the regions to be inspected. A specific method of determining such regions is as follows: Dummy pattern regions are first identified since they need not be inspected. Specifically, from the result of pattern grouping, it is determined whether there exists a group of dummy patterns. If such a group is determined to exist, that group is designated. The coordinates of each defect point contained in the group are regarded as the center of a field of view, and the regions each having the same size as that field of view are regarded as individual dummy pattern regions. Each of the individual dummy pattern regions is inspected for all defects contained in the group, and the regions with the dummy patterns are added up to make up an ultimate dummy pattern region. Next, the regions to be inspected for defects inside and outside the partial regions, or the regions to be inspected in terms of defect type are determined. The regions subject to inspection have their different contents established depending on the result of data classification. For example, if the defects found inside a partial region are determined to be insignificant as the data of any defect type, the inspection inside the partial region is regarded as unnecessary, and another region other than that partial region is set as the next region to be inspected. If there is found inside a partial region a high incidence of defects whose type is important from the viewpoint of yield management, that partial region is set as the region to be inspected because it is necessary to monitor the incidence trend of these defects. Ultimately, the regions to be inspected minus the dummy pattern regions are determined to be the regions to be inspected and are output as such to the YMS 1003. The above process is performed on each of the regions (5 regions in the example shown in FIG. 11) set on the wafer.

FIGS. 12A and 12B show typical chip maps prepared of different regions set on the wafer, the domains of high defect concentration being different from one region to another. In such a case, the ultimately established regions to be inspected are highly likely to be different domains established from one region to another on the wafer. For example, with regard to the chips on the top right side of the wafer circumference, the circuit pattern regions on that side might be set as the regions to be inspected; and regarding the chips on the top left side of the wafer circumference, the circuit pattern regions on that side might also be set as the regions to be inspected.

The regions to be inspected that are output by the system involved with the second embodiment are not limited to the regions already inspected by the wafer inspection tool, and may include yet-to-be-inspected regions. For this reason, when the regions set as described above for inspection are inspected by the SEM type wafer inspection tool 1013, there is an increased possibility that those defects not detected by the optical wafer inspection tool 0001 will be detected.

The inspection region information obtained in the above-described manner is output to and stored into the YMS 1003 (S204). The inspection region information may be used in evaluating the process conditions and design circuit patterns in process development work. Since the information about the determined regions is the region information regarding an intra-chip coordinate system, the chips to be measured need to be identified when the wafer is to be actually measured. For example, if the wafer used in determining the regions to be inspected is further subjected to reacquisition of images, the chips targeted for inspection are designated, and the regions to be inspected in the wafer coordinate system are calculated from the coordinates of the origin of the chips on the wafer and from intra-chip area information about the obtained regions to be inspected.

The output inspection region information may also be used as production monitoring positions for mass-producing the device in question. That is, the inspection region information registered in the YMS 1003 at the stage of process development may be used to perform partial region inspection during the stage of mass production for production monitoring purposes.

The preceding paragraphs explained an example in which the coordinates of the positions of defect candidates on the wafer are obtained by the optical inspection tool. However, this is obviously not limitative of the present invention when it is embodied.

For example, the coordinates of the positions of defect candidates may also be acquired using a SEM type inspection tool besides the optical inspection tool. As discussed above, the throughput of the SEM type inspection tool is drastically lower than that of optical inspection tools, so that it is practically impossible to inspect the entire surface of the wafer by SEM type inspection. Still, SEM type inspection tools recently made available provide enhanced throughput, and some of them have a mode in which their sensitivity of inspection is lowered in order to attain higher throughput. Thus even though it is unworkable to inspect the whole surface of the wafer by the SEM type inspection tool, it is possible to inspect a certain area (e.g., 1/100 of the chip area) thereby. It is therefore feasible to limit the regions of interest in this manner, identify the positions of defect candidates in the limited regions by SEM type inspection, and isolate the region to be inspected in more detail using the inspection region determination method or apparatus described in connection with this embodiment.

As explained so far, in order to isolate the region to be inspected in detail, an image corresponding to each of the defect candidate positions is first acquired; various attributes are calculated from the images and from the coordinate values thus obtained; and the region to be inspected is identified as the inspection position identification information based on these attributes. Alternatively, it is also possible to determine the regions to be measured and inspected as the inspection position identification information from the coordinate data without acquiring images. For example, a map may be prepared by overlaying the acquired positions of defect candidates on a plurality of chips, and the regions to be inspected may be determined only from the map information. Specifically, as shown in FIG. 5B, it is possible to identify the regions of high defect concentration from the chip layout and to set them up as the regions to be inspected. To inspect one of such regions thus identified requires dividing the region into a plurality of field-of-view sizes in order to obtain images of the region a number of times. If there exist the positions of the region (e.g., if the region is rectangular, the intra-chip coordinates of its four corners are the positions) and information about the field-of-view size for imaging, it is easy to calculate the positions to be imaged.

It is also to be expected that the region to be inspected may not be where defect concentration is very high on the prepared map. That is, even where the reliability of extracted defects in the defect candidate positions is low and where the defect concentration in the region concerned is low on the map, if the presence of true defects is suspected, that region of low deficit concentration might be designated as the region to be measured and inspected.

(Third Embodiment)

The third embodiment is an extension of the first embodiment of the present invention targeted for the lithography process. In connection with the first embodiment, it was explained that the FEM wafer is inspected by the wafer inspection tool and that the result of the inspection is regarded as defect candidate positions which are subjected to the SEM review. Meanwhile, recent advances in process simulation technology have made it possible to predict, to a certain extent by simulation, how the circuit pattern shape varies when the process conditions have been changed in the wafer process. For example, with regard to the lithography process, inputting the design layout data of the circuit pattern, exposure conditions (focus and dose), the resist material, etc., to an exposure simulator makes it possible to obtain a predicted pattern shape to be exposed. Utilizing this simulator enables prediction of those changes in the pattern shape which are attributable to process variations. It is thus possible to predict where a pattern change can occur when the process conditions vary and in what manner the change of the shape takes place (pattern-short, pattern-open, etc.). The region to be measured is then determined based on the information about the defect candidate positions as the defect attribute information to be output from that simulator.

Figure 14:
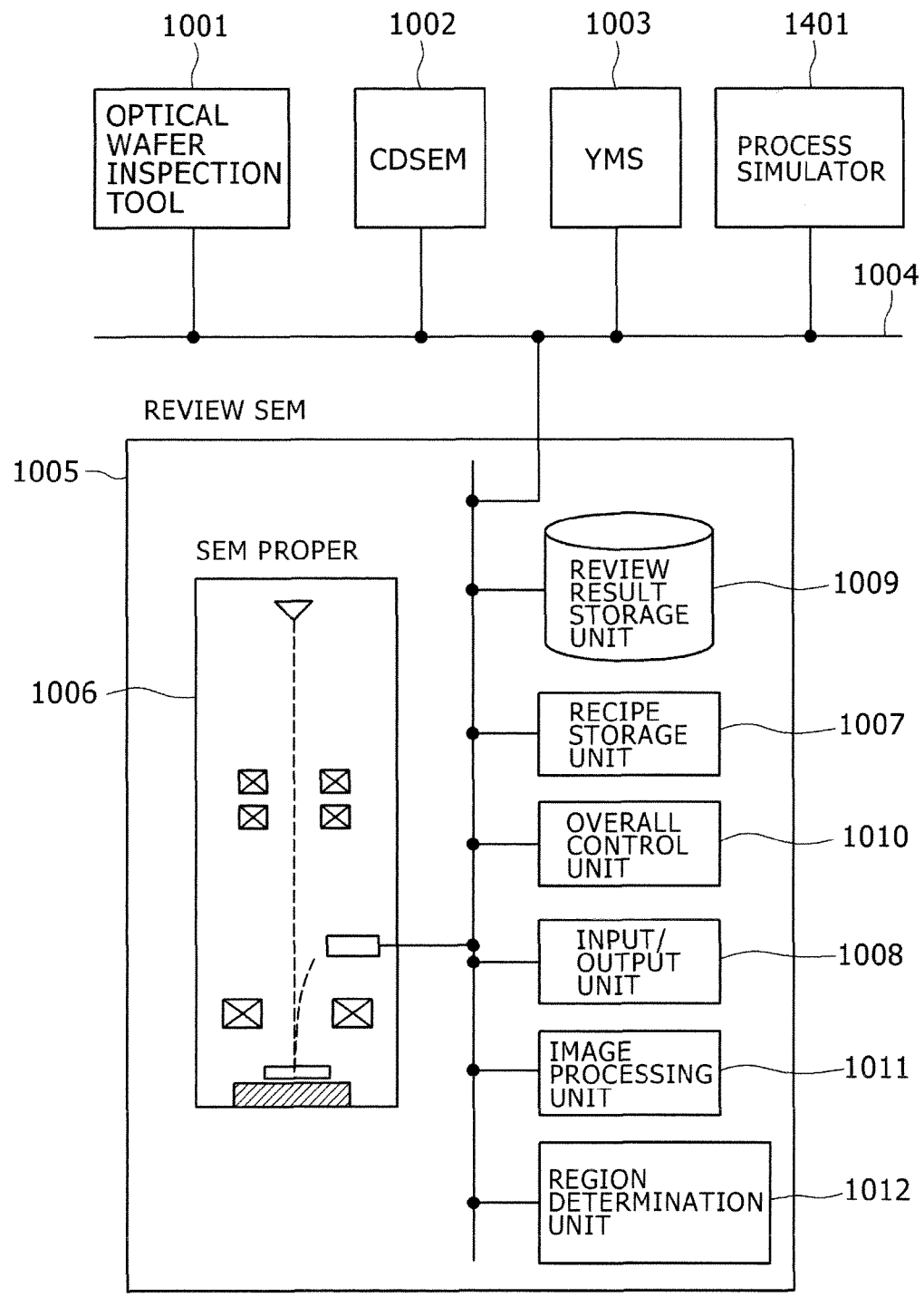
FIG. 14 is a general view of an inspection system involved with a third embodiment of the present invention.
Figure 15:
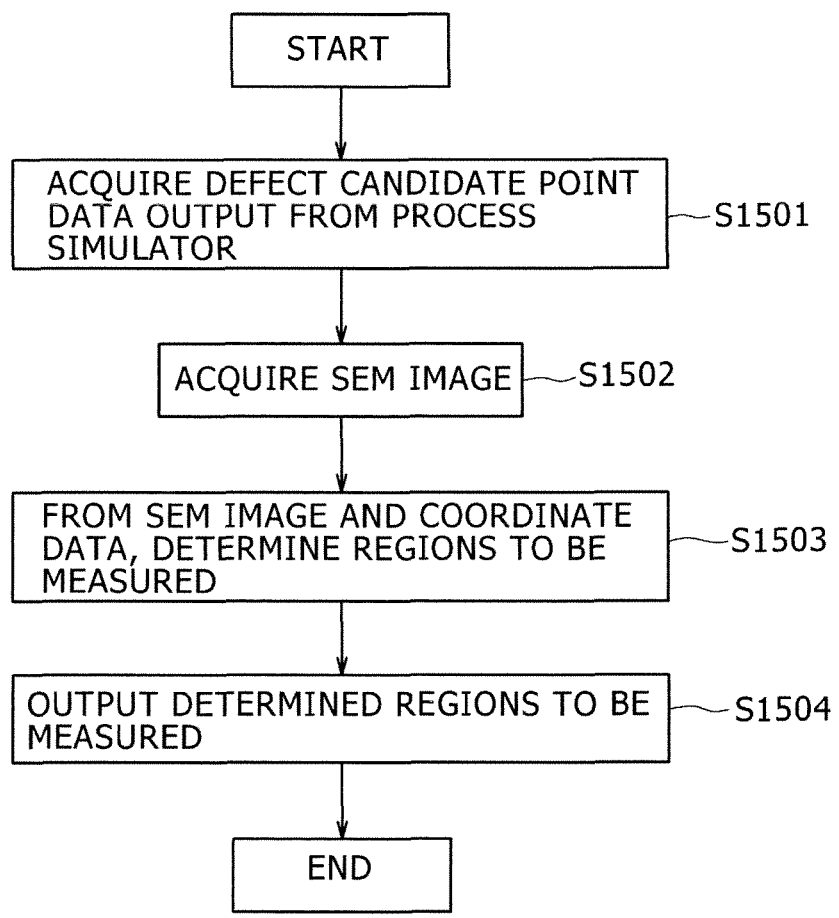
FIG. 15 depicts a process flow of the third embodiment.

FIG. 14 is a block diagram of this system. The block diagram of FIG. 14 differs from that of FIG. 1 in that a process simulator (exposure simulator) 1401 is connected to the network 1004. FIG. 15 shows the process flow of this system.

It is assumed that there is prepared beforehand an FEM wafer with its circuit patterns of the target device fabricated by changing the exposure conditions from one chip to another. First, the target circuit pattern layout is input to the process simulator 1401 to obtain the intra-chip coordinate data of the defect candidate positions on the circuit patterns (S1501). Then the chip targeted for evaluation is designated on the FEM wafer, and a SEM image corresponding to the defect candidate positions on the designated chip is obtained (S1502). Also, a reference image corresponding to each defect candidate position is acquired from other chips in a satisfactorily processed state, as with the first embodiment. Thereafter, the regions to be measured are determined as the inspection position identification information from the defect data (intra-chip coordinates, chip ID, SEM image) (S1503). The regions thus determined for measurement are output to the YMS 1003 (S1504). The specific details of the process of determining the regions to be measured are substantially the same as explained in connection with the first embodiment. The difference is that the coordinate data accompanying each defect represents coordinate values in the design layout data. For this reason, there are no errors such as those in the coordinate positions obtained by the optical wafer inspection tool. There is thus no need for coordinate correction through pattern matching between the SEM image and the design layout data.

The foregoing explanation gave an example in which numerous defect candidates output from the exposure simulator are submitted to the CDSEM 1002 which in turn determines the positions to be measured using review images. The same concept applies not only to the lithography process but also to other processes as well. SEM images regarding the coordinate values of the positions where defects are likely to occur may be acquired by any of various process simulators or the like using a wafer prepared in the actual process. The acquired SEM images may then be used to furnish attributes to the defects. On the basis of the defect attributes thus furnished, the positions to be inspected or measured may be determined as the inspection position identification information.

(Fourth Embodiment)

Discussed so far have been the systems for identifying the positions to be measured or the regions to be inspected based on the SEM review images corresponding to the defect candidate positions. Explained hereunder as the fourth embodiment is a system that realizes enhanced efficiency in SEM review in cases where there exist a large number of defect candidate positions.

Figure 16:
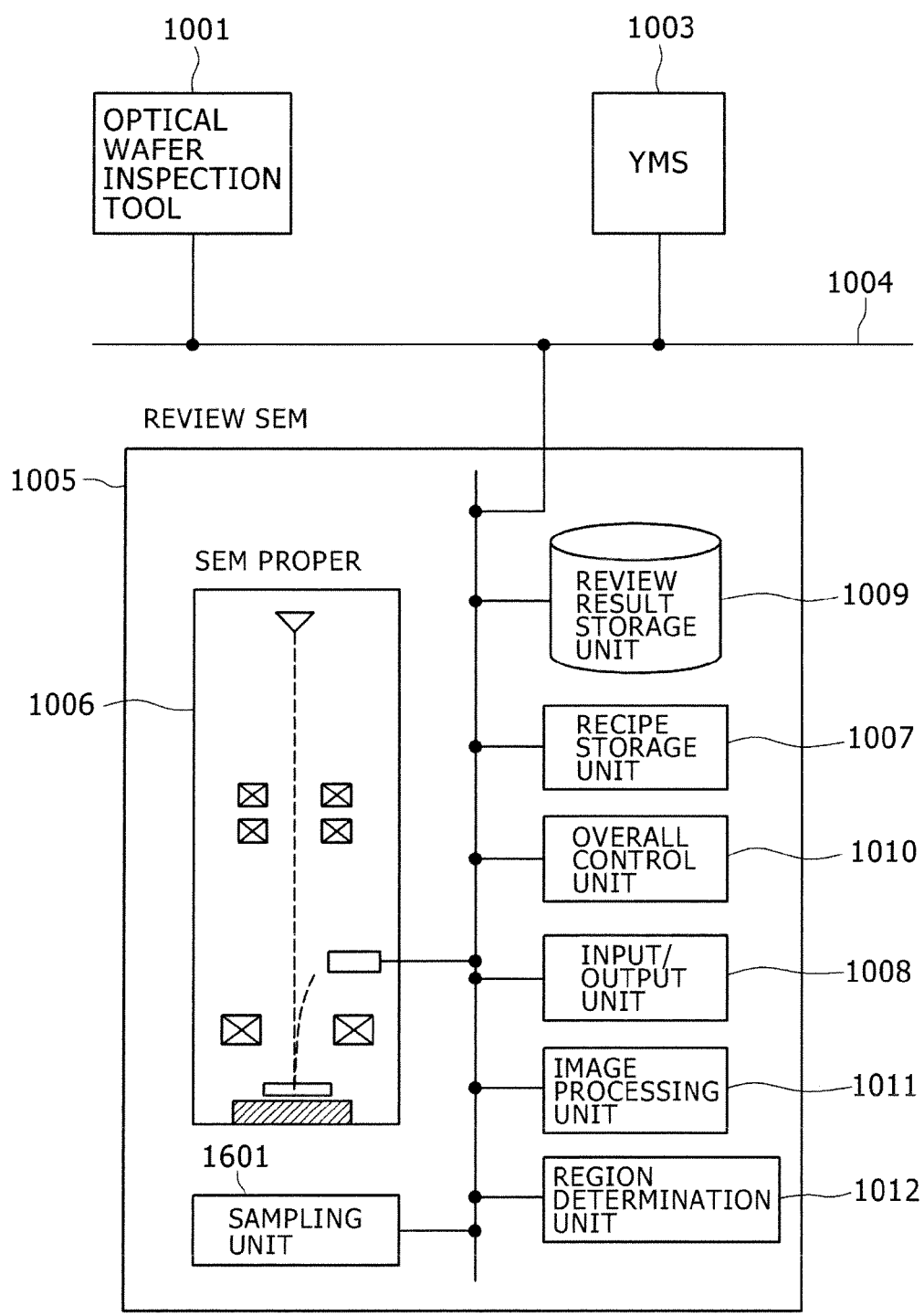
FIG. 16 is a general view of an inspection system involved with a fourth embodiment of the present invention.
Figure 17:
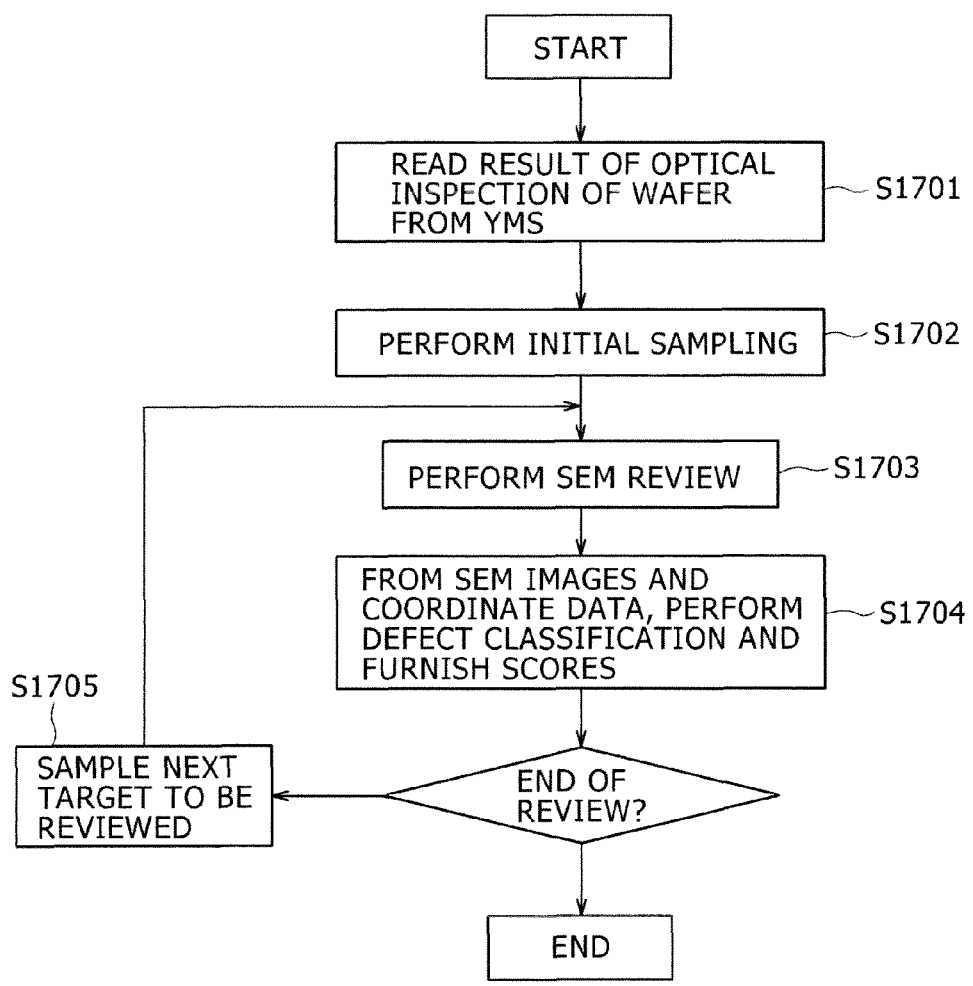
FIG. 17 depicts a process flow of the fourth embodiment.

The characteristic of the fourth embodiment lies in promoting efficiency in acquiring the images of the numerous defect candidate position coordinates obtained by the wafer inspection tool or by the simulator. The SEM review is carried out in multiple steps in combination with the sampling process; not all positions are imaged at one time in a single review process. FIG. 16 is a block diagram of this system. The block diagram of FIG. 16 differs from that of FIG. 1 in that a sampling unit 1601 is added inside the review SEM 1005. The sampling unit has the function of sampling as many points as will be actually submitted to SEM review given the defect candidate information input from the YMS 1003. The sampling unit also is also characterized by the function of performing the sampling process based on the detailed positions to be measured or regions to be inspected as determined by the region determination unit 1012. FIG. 17 shows the process flow of this system.

First, the data on the defect candidate positions is read from the YMS 1003 (S1701). The sampling unit 1601 then performs an initial sampling process (S1702). The initial sampling involves selecting partial data from large quantities of defect candidate data. In this case, the defects are sampled in such a manner that the ratio of the defect count between chips on the wafer will not vary significantly before and after the sampling in order to grasp the defect incidence trend over the entire wafer surface. For example, if the data count after sampling is set for 50% of the total number of defect candidates, the defects are randomly sampled from each of the chips with the same ratio of defects (50% in this example). Next, SEM images of the sampled defect candidates are obtained (S1703). Given the result of the review, the defect classification process is carried out along with the furnishing of scores in the same manner as discussed above in conjunction with the first, the second, and the third embodiments (S1704). The review result means that the trend of defect incidence over the wafer in question has been analyzed using the sampled defects. That is, using the sampling data, information is obtained about the intra-chip positions where defect concentration is high, about the characteristic circuit pattern shapes in which defects are found, about the types of the defects taking place, and the positions where dummy patterns exist.

If there still remain a large number of defects yet to be reviewed at this point, the view is continued. In such a case, based on the result of the analysis of the defects obtained so far, the positions of the defects to be subjected next to SEM review are sampled from the yet-to-be-reviewed positions (S1705). A specific sampling method may involve excluding from the next round of sampling the yet-to-be-reviewed positions in the already-known dummy pattern regions. Furthermore, it is determined that the positions already determined to have defect concentration need no further review and that these regions are excluded from the next round of sampling. The data to be reviewed next is then sampled from the yet-to-be-reviewed data minus the samples to be excluded. This type of sampling, unlike the initial sampling, does not necessarily require that the defect candidate count be the same from one chip to another. The defect positions thus sampled are again submitted to SEM review (S1703). And again on the basis of the result of the SEM review, each of the defect images is classified and furnished with a score (S1704). Repeating the above process makes it possible to acquire the result of the SEM review regarding the defects to be verified while excluding the dummy pattern regions from the review and avoiding acquisition of a more-than-necessary number of image data regarding the positions where large quantities of defects have locally occurred.

From the review result thus obtained, the regions to be inspected are determined and output as the inspection position identification information as discussed above in conjunction with the first through the third embodiments.

(Fifth Embodiment)

Described below as the fifth embodiment is a review apparatus capable of setting the regions to be measured or inspected as the inspection location identification information based on the review images corresponding to the defect candidate positions, and of measuring or inspecting the set regions using the same apparatus.

Figure 18:
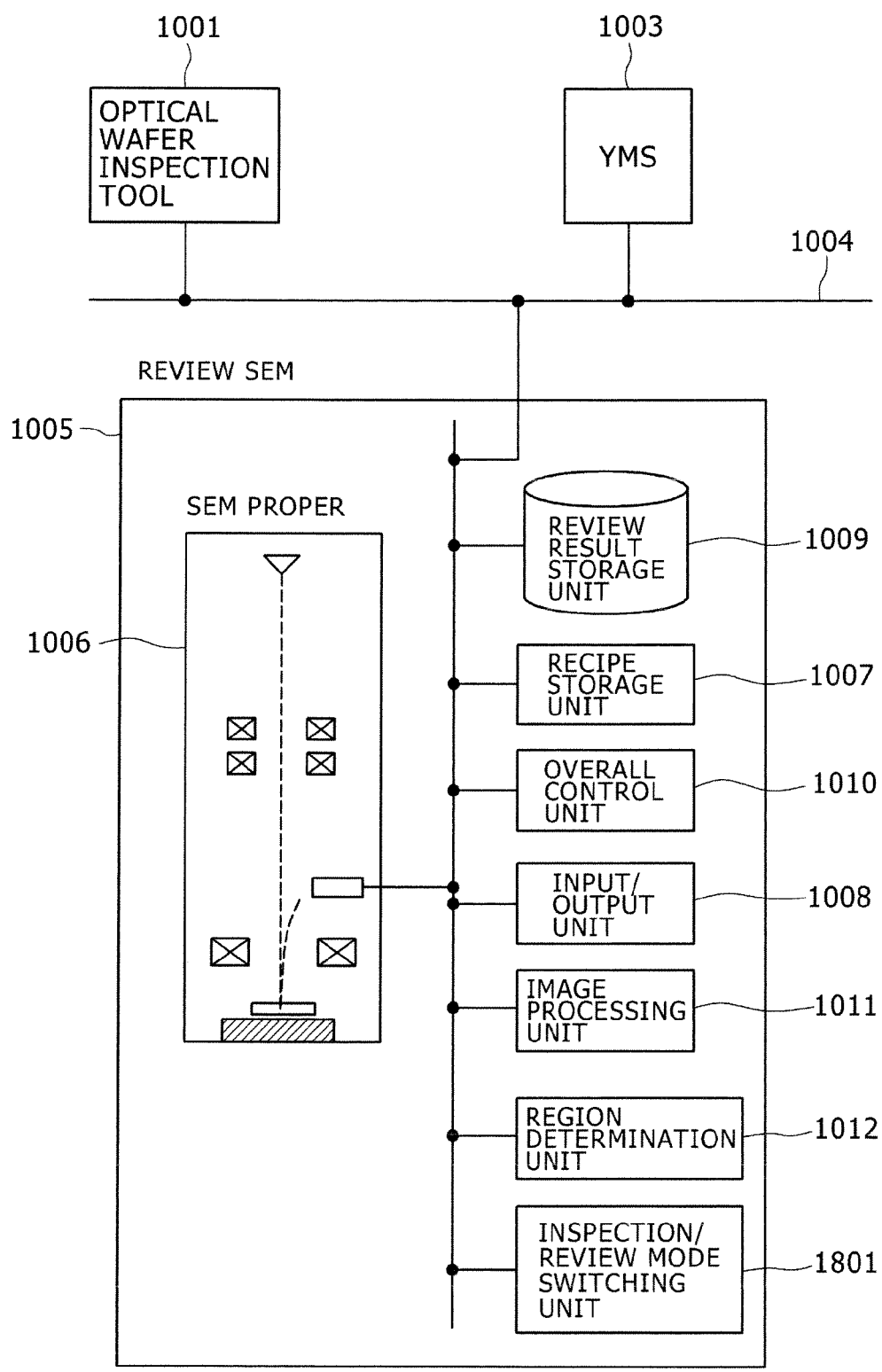
FIG. 18 is a general view of an inspection system involved with a fifth embodiment of the present invention.

FIG. 18 shows an inspection system including a review SEM involved with the fifth embodiment. The setup of FIG. 18 differs in particular from that of FIG. 1 in that an inspection/review mode switching unit 1801 acting as a processing mode switching unit is added inside the review SEM 1005. The inspection/review mode switching unit 1801 incorporated in the review SEM 1005 has the function of switching the processing mode of the review SEM 1005 between inspection mode in which the defect inspection process is performed on the one hand, and review mode in which the defect review is carried out on the other hand. Inspection mode and review mode are functionally the same when they permit the SEM proper 1006 to obtain SEM images and allow the image processing unit 1011 to perform the defect detection process. However, the two modes differ from each other in terms of various process conditions. In inspection mode, it is required that the target regions as the predetermined inspection position identification information be inspected under the conditions conducive to the highest possible throughput. For example, the number of frames for averaging may be set to about two, with the amount of the probe current set to about 1 nA. Also, a wide field of view may be acquired by setting the imaging field of view to several micrometers in size. The purpose of view mode, on the other hand, is to acquire high-resolution images of defect candidate coordinates. Given that purpose, the probe current may be set to about 100 pA, and the number of frame for averaging may be set to, say, 32 to obtain images with high S/N ratios. These conditions are stored in the recipe storage unit 1007. The inspection/review mode switching unit 1801 orders the overall control unit 1010 to switch these imaging conditions. In turn, the overall control unit sets the imaging conditions from the recipe storage unit 1007 to the SEM proper 1006 or to the image processing unit 1011 so as to acquire images and to perform the process in accordance with each mode in effect.

Figure 19:
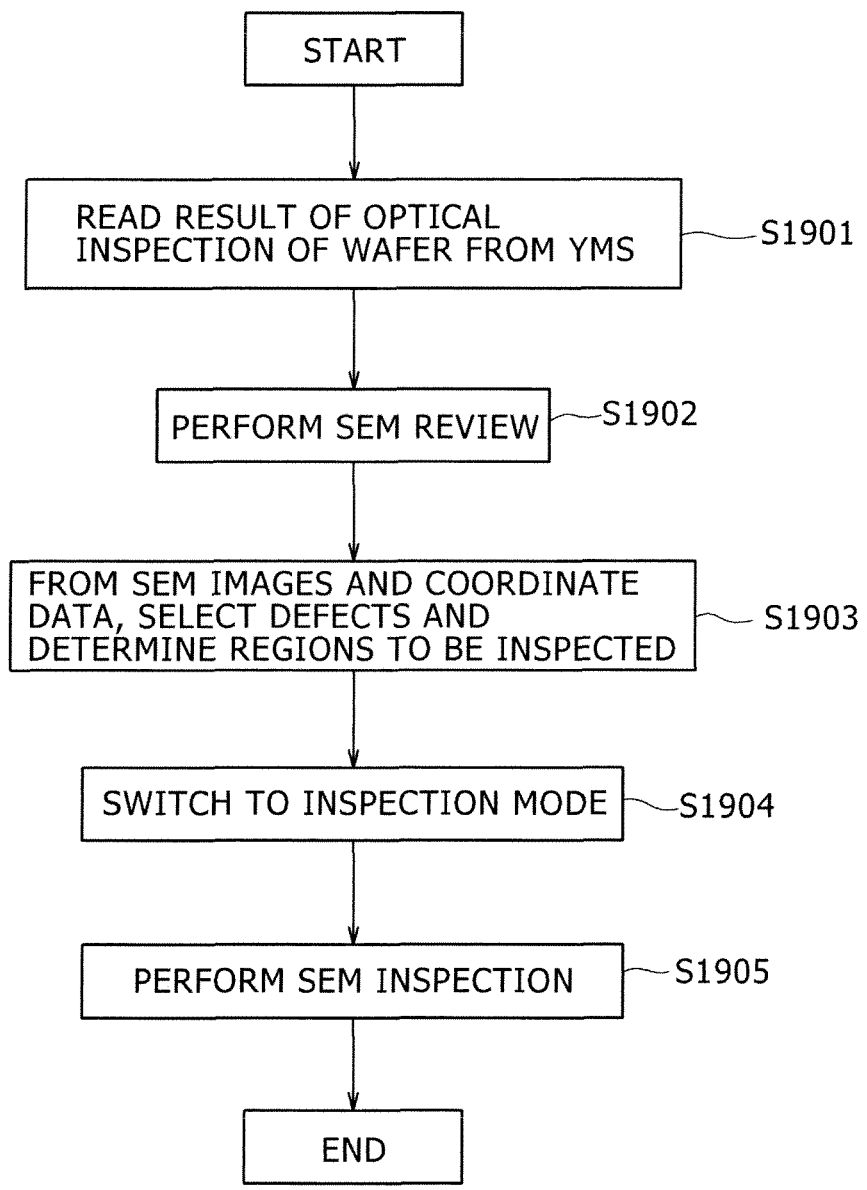
FIG. 19 depicts a process flow of the fifth embodiment.

FIG. 19 is a flowchart showing how the fifth embodiment works. At the start of the process, the review SEM 1005 is assumed to be set in review mode. First, the result of appearance inspection performed over an extensive area of the wafer by the optical wafer inspection tool or the like is acquired from the YMS 1003 (S1901). A SEM review is performed on the defect positions (S1902). Then using the acquired data (chip IDs, intra-chip coordinates, SEM images), the region determination unit 1012 determines the regions to be inspected as inspection position identification information (S1903). Next, the inspection/review mode switching unit 1801 orders the entire control unit 1010 to set the conditions for carrying out the inspection process with the SEM proper 106 and image processing unit 1011 (S1904). Thereafter, the regions thus determined are inspected for defects (S1905).

The obtained result of the inspection and that of the measurement are output to the YMS 1003 in the form of inspection result files. Given these results, the review SEM 1005 can also perform SEM review in review mode for the purpose of more detailed analysis. Although what was discussed above was an example of carrying out defect inspection, pattern measurement may also be performed in like manner.

(Other Embodiments)

Whereas the first through the fifth embodiments discussed so far are also included in its scope, the present invention may be embodied particularly in the form of an apparatus having functionality to determine partial regions on the wafer for pattern measurement, observation and inspection; a method for determining such partial regions; or a defect review apparatus having such a region determination function, each embodiment being for use when the entire wafer surface cannot be targeted for evaluation from the viewpoint of throughput (e.g., when pattern measurement and defect inspection are carried out using an electron beam apparatus serving as a charged particle beam apparatus). For example, if pattern measurement and observation and defect inspection are carried out not over the entire specimen surface but on partial regions thereon using an electron beam apparatus, the embodiment may be used efficiently to determine the partial regions subject to pattern measurement and observation or defect inspection when: (1) it is difficult to predict the positions to be measured, observed or inspected (positions prone to defects); or (2) even if information about defect-prone positions is obtained by some appropriate means, that information is a mixture of information about true defects and information about false defects.

As another embodiment of the present invention, there may be provided an apparatus and a method for use given the information about those positions on the wafer which are liable to develop defects or given the information about such positions along with the image data for imaging those positions, the apparatus and method being used to extract the features of the positions likely to develop true defects and to identify the partial regions to be subjected to pattern measurement and observation and defect inspection based on the extracted features. The apparatus and method of this embodiment are characterized in that the features of the defect-prone positions are defined using the positions of the chips where defects have actually occurred, the intra-chip coordinates of the defect positions, the information about the type of the defects having occurred, and the attribute information about the circuit pattern shapes of the positions where the defects have developed.

As another embodiment of the present invention, there may be provided a defect review apparatus acting as an observation apparatus or an inspection tool having the function of obtaining images corresponding to those positions on the wafer which are likely to develop defects and of which the position information has been input, as well as the function of identifying the regions to be inspected from the position information and image information about those defects.

As another embodiment of the present invention, there may be provided an apparatus having the function of obtaining images corresponding to those positions on the wafer which are likely to develop defects and of which the position information has been input, the function of identifying the regions to be inspected from the position information and image information about those defects, and the function of inspecting the identified regions, i.e., an electron beam type review apparatus having both the review function and the inspection function.

According to the above embodiment, when it is difficult empirically to predict the regions where defects occur, or when the information about the positions of true defects to be inspected tends to be mixed with the information about large quantities of false defects despite the availability of other means capable of detecting defect-prone position candidates, it is possible efficiently to determine the partial regions to be measured for patterns or inspected for defects. Because only the determined regions are inspected for defects or are measured for patterns using the electron beam apparatus, defect management and process management can be conducted efficiently.

Also, according to the review apparatus having both the function of obtaining images corresponding to those positions on the wafer which are likely to develop defects and of which the position information has been input and the function of identifying the regions to be inspected from the position information and image information about those defects, if there exist a large number of those positions on the wafer which are likely to develop defects, it is possible to obtain images corresponding to the positions using partial data thereof, extract the features of defect-prone regions based on the image data, select from the data of yet-to-be-imaged defect candidates the data of the defect candidate positions coinciding with the extracted information, and acquire images only of the selected data. In this manner, given the input defect candidate data, there is no need to acquire the image data of all positions at one time. This permits efficient acquisition of images.

Furthermore, according to the apparatus having the function of obtaining images corresponding to those positions on the wafer which are likely to develop defects and of which the position information has been input, the function of identifying the regions to be inspected from the position information and image information about those defects, and the function of inspecting the identified regions, a single apparatus can obtain images corresponding to the defect candidate positions, identify the defect-prone positions, and inspect the identified positions in a continuous manner thereby providing the effect of shortening the time required to obtain the ultimate inspection result.

DESCRIPTION OF REFERENCE CHARACTERS

1001 Optical wafer inspection tool
1002 CDSEM
1003 YMS
1004 Network
1005 Review SEM
1006 SEM proper
1007 Recipe storage unit
1008 Input/output unit
1009 Review result storage unit
1010 Overall control unit
1011 Image processing unit
1012 Region determination unit
1013 SEM type wafer inspection tool
1014 Layout analysis unit
1015 Layout CAD data
1401 Process simulator
1601 Sampling unit
1801 Inspection/review mode switching unit
3001 Attribute furnishing unit
3002 Score calculation unit
3003 Data classification unit
3004 Region output unit

The invention claimed is:

1. A region-of-interest determination apparatus comprising an image processor configured to:
 calculate a degree of a defect based on at least a plurality of kinds of defect attribute information regarding defect data, the defect data including an image corresponding to a defect position detected on a specimen by inspection thereof or an image corresponding to a defect position predicted to be likely to develop a defect on the specimen, both images being obtained by imaging; and
 extract the defect data of which the degree is higher than a predetermined level, and determine a region to be observed or inspected on the specimen based on the extracted defect data,
 wherein at least one of said plurality of kinds of defect attribute information is pattern grouping information about the defect data.

2. The region-of-interest determination apparatus according to claim 1, wherein at least one of said plurality of kinds of defect attribute information is classification information about a defect type.

3. The region-of-interest determination apparatus according to claim 1, wherein at least one of said plurality of kinds of defect attribute information is information about a chip position of said defect on the specimen or information about an intra-chip position of said defect.

4. An observation apparatus or an inspection apparatus comprising:
 the region-of-interest determination apparatus according to claim 1, wherein:
 the image processor is further configured to acquire acquires an image corresponding to said defect position based on information about the determined region.

5. The observation apparatus or the inspection apparatus according to claim 4, wherein at least one of said plurality of kinds of defect attribute information is classification information about a defect type.

6. The observation apparatus or the inspection apparatus according to claim 4, wherein at least one of said plurality of kinds of defect attribute information is information about a chip position of said defect on the specimen or information about an intra-chip position of said defect.

7. The observation apparatus or the inspection apparatus according to claim 4, wherein the image processor is further configured to:
 switch a process mode between a defect inspection process mode in which a defect inspection process is performed and a defect review process mode in which a defect review process is carried out; and inspect the region is determined in the defect review process mode, the determined region in the defect inspection process mode.

8. An observation apparatus or an inspection apparatus comprising an image processor configured to:
- calculate a degree of a defect based on at least a plurality of kinds of defect attribute information regarding defect data, the defect data including an image corresponding to a defect position detected on a specimen by inspection thereof or an image corresponding to a defect position predicted to be likely to develop a defect on the specimen, both images being obtained by imaging;
- extract the defect data of which the degree is higher than a predetermined level, and determine a region to be observed or inspected on the specimen based on the extracted defect data;
- acquire an image corresponding to said defect position based on information about the determined region; and
- sample, based on the information about the region determined, the defect data from the defect position on the specimen or from the position predicted to be likely to develop the defect on the specimen.

9. A region-of-interest determination method comprising steps of:
- calculating a degree of a defect based on at least a plurality of kinds of defect attribute information regarding defect data, the defect data including an image corresponding to a defect position detected on a specimen by inspection thereof or an image corresponding to a defect position predicted to be likely to develop a defect on the specimen, both images being obtained by imaging; and
- extracting the defect data of which said degree is higher than a predetermined level, and determining a region to be observed or inspected on the specimen based on the extracted defect data,
- wherein at least one of said plurality of kinds of defect attribute information is pattern grouping information about the defect data.

10. An observation method or an inspection method comprising the step of determining the region on the specimen using the region-of-interest determination method according to claim 9, and observing or inspecting said determined region.

11. An observation method or an inspection method comprising the steps of:
- determining the region on the specimen using the region-of-interest determination method according to claim 9, and selecting a defect coordinate position from which to acquire image data based on information about said determined region; and
- acquiring the image data from the selected defect coordinate position.

12. The method according to claim 9, wherein at least one of said plurality of kinds of defect attribute information is classification information about a defect type.

13. The method according to claim 9, wherein at least one of said plurality of kinds of defect attribute information is information about a chip position of said defect on the specimen or information about an intra-chip position of said defect.

14. The method according to claim 9, further comprising:
- sampling, based on the information about the region determined, defect data from the defect position on the specimen or from the position predicted to be likely to develop the defect on the specimen.

15. The method according to claim 9, further comprising:
- switching a process mode between a defect inspection process mode in which a defect inspection process is performed and a defect review process mode in which a defect review process is carried out; and
- inspecting, after the determining the region in the defect review process mode, the determined region in the inspection process mode.

* * * * *